United States Patent
Inman et al.

(10) Patent No.: US 6,552,085 B2
(45) Date of Patent: Apr. 22, 2003

(54) COMPOSITIONS CONTAINING HYPOGLYCEMICALLY ACTIVE STILBENOIDS

(75) Inventors: Wayne D. Inman, San Luis Obispo, CA (US); David C. Hopp, Mill Creek, WA (US)

(73) Assignee: Insmed Incorporated, Glen Allen, VA (US)

( * ) Notice: Subject to any disclaimer, the term of this patent is extended or adjusted under 35 U.S.C. 154(b) by 16 days.

(21) Appl. No.: 09/919,883

(22) Filed: Aug. 2, 2001

(65) Prior Publication Data

US 2002/0058701 A1 May 16, 2002

Related U.S. Application Data

(60) Provisional application No. 60/225,665, filed on Aug. 16, 2000.

(51) Int. Cl.$^7$ ..................... A61K 31/185; A61K 31/075
(52) U.S. Cl. ........................................ 514/576; 514/718
(58) Field of Search .................................. 514/576, 718

(56) References Cited

U.S. PATENT DOCUMENTS

| | | | |
|---|---|---|---|
| 5,827,898 A | 10/1998 | Khandwala et al. | ........ 514/734 |
| 5,830,887 A | * 11/1998 | Kelly | ........................ 514/182 |

FOREIGN PATENT DOCUMENTS

| | | |
|---|---|---|
| WO | WO 99/56737 A1 | 11/1999 |
| WO | WO 00/26167 A1 | 5/2000 |
| WO | WO 00/69430 A1 | 11/2000 |
| WO | WO 01/42231 A2 | 6/2001 |
| WO | WO 02/13806 A2 | 2/2002 |
| WO | WO 02/13809 A2 | 2/2002 |
| WO | WO 02/13811 A2 | 2/2002 |

OTHER PUBLICATIONS

Arichi, H., et al., "Effects of Stilbene Components of the Roots of *Polygonum cuspidatum* SIEB. et Zucc. on Lipid Metabolism," *Chem. Pharm. Bull. 30*:1766–1770, Pharmaceutical Society of Japan (1982).

Bhattacherjee, P., et al., "The Effects of a Novel Series of Selective Inhibitors of Arachidonate 5–Lipoxygenase on Anaphylactic and Inflammatory Responses," *Ann. N.Y. Acad. Sci. 524*:307–320, New York Academy of Sciences (1988).

Cooksey, C.J., et al., "Two Novel Stilbebe–2–Carboxylic Acid Phytoalexins from *Cajanus cajan*," *Phytochemistry 21*:2935–2938, Pergamon Press Ltd. (1982).

Devi, K.S. and Kurup, P.A., "Effects of Certain Indian Pulses on the Serum, Liver and Aortic Lipid Levels in Rats Fed a Hypercholesterolaemic Diet," *Atherosclerosis 11*:479–484, Elsevier Publishing Company (1970).

Fauconneau, B., et al., "Comparative Study of Radical Scavenger and Antioxidant Properties of Phenolic Compounds from *Vitis vinifera* Cell Cultures Using In Vitro Tests," *Life Sci. 61*:2103–2110, Elsevier Science Inc. (1997).

Goda, Y., et al., "Inhibitors of the Arachidonate Cascade from *Allium chinense* and Their Effect on in Vitro Platelet Aggregation," *Chem. Pharm. Bull. 35*:2668–2674, Pharmaceutical Society of Japan (1987).

Gowri, M.S., et al., "Masoprocol decreases rat lipolytic activity by decreasing the phosphorylation of HSL," *Am. J. Physio. Endocrinol. Metab. 279*:E593–E600, American Physiological Society (Sep. 2000).

Gryglewski, R.J. and Eckstein, M., "Fibrinolytic Activity of some Biarylcarboxylic Acids," *Nature 214*:626, Macmillian Journals Ltd. (1967).

Hedberg, I., et al., "Inventory of Plants Used in Traditional Medicine in Tanzania. Part III. Plants of the Families Papilionaceae–Vitaceae," *J. Ethnopharm. 9*:237–260, Elsevier Scientific Publishers Ireland Ltd. (1983).

Jahromi, M.A.F. and Ray, A.B., "Antihyperlipidemic Effect of Flavonoids from *Pterocarpus marsupium*," *J. Nat. Prod. 56*:989–994, American Society of Pharmacognosy (1993).

Matsuda, H., et al., "Structure–Requirements of Isocoumarins, Phthalides, and Stilbenes from Hydrangeae Dulcis Floium for Inhibitory Activity on Histamine Release from Rat Peritoneal Mast Cells," *Bioorg. Med. Chem. 7*:1445–1450, Elsevier Science Ltd. (Jul. 1999).

Pending Non–Provisional U.S. patent application No. 09/919,966, Hoppe et al., filed Aug. 2, 2001.

Amalraj, T., and Ignacimuthu, S., "Hypoglycemic activity of *Cajanus cajan* (seeds) in mice," *Indian J. Exp. Biol.* 36: 1032–1033, Council of Scientific & Industrial Research (1998).

Asakawa, Y., et al., "Prenyl Bibenzyls from the Liverworts *Radula perrottetii* and *Radula complanata*," *Phytochemistry 30*:235–251, Pergamon Press (1991).

Asakawa, Y., et al., "Prenyl Bibenzyls from Liverwort *Radula kojana*," *Phytochemistry 30*:219–234, Pergamon Press (1991).

Avella, M.E., et al., "Evaluacion de la Medicina Tradicional: Efectos de *Cajanus cajan* L. (Guandu) y de *Cassia fistula* L. (Cañafistula) en el Metabolismo de los Carbohidratos en el Raton," *Rev. Méd. Pan. 16*:39–45, Revista Medica De Panama (1990).

Boonlaksiri, C., et al., "An antimalarial stilbene from *Artocarpus integer*," *Phytochemistry 54*:415–417, Elsevier Science Ltd. (Jun. 2000).

(List continued on next page.)

Primary Examiner—Raymond Henley, III
(74) Attorney, Agent, or Firm—Sterne, Kessler, Goldstein & Fox LLP

(57) ABSTRACT

The use of isolated or purified stilbenoid compounds including longistyline A-2-carboxylic acid as hypoglycemic agents or to lower serum glucose levels is described. The invention also relates to the use of such stibenoid compounds in combination with other hypoglycemic agents.

11 Claims, 6 Drawing Sheets

OTHER PUBLICATIONS de Lima, O.G., et al., "Substâncias Antimicrobianas de Plantas Superiores. Comunicação XLVI. Primeiras Observações Sobre os Efeitos Biológicos de Extratos de Córtex do Caule e Raízes de Balchê, *Lonchocarpus violaceus* (Jacq.) D.C. (=L. longistyllus Pittier), a Planta Mítica dos Maias do México, da Guatemala e das Honduras (Britânicas)," *Revista do Instituto de Antibióticos* 15:3–15, Departamento de Botânica da Universidade Nacional do México (1975).

Manickam, M., et al., "Antihyperglycemic Activity of Phenolics from *Pterocarpus marsupium*," *J. Nat. Prod.* 60:609–610, American Chemical Society and American Society of Pharmacognosy (1997).

Mitscher, L.A., et al., "Amorfrutin A and B, Bibenzyl Antimicrobial Agents from *Amorpha fruticosa*," *Phytochemistry* 20:781–785, Pergamon Press (1981).

Mitscher, L.A., et al., "Antimicrobial Agents from Higher Plants: Prenylated Flavonoids and Other Phenols form *Glycyrrhiza lepidota*," *Phytochemistry* 22:573–576, Pergamon Press Ltd. (1983).

Shimizu, K., et al. "The Inhibitory Components from *Artocarpus incisus* on Melanin Biosynthesis," *Planta Med.* 64:408–412, Georg Thieme Verlag Stuttgart (1998).

Viswanahan, M., et al., "Responses to Legumes in NIDDM Subjects: Lower Plasma Glucose and Higher Insulin Levels," *Nutr. Rep. Int.* 40:803–812, Elsevier Science (1989).

International Search Report for PCT/US01/25382, Hopp, D.C., mailed Jun. 28, 2002.

Chemical Abstracts Database, Accession No. 93:37284, Cotias, C., et al. (1979).

Napralert Database, Accession No. 95:6363, Chen, D.H., et al. (1985).

* cited by examiner

COMPOSITIONS CONTAINING HYPOGLYCEMICALLY ACTIVE STILBENOIDS

CROSS-REFERENCE TO RELATED APPLICATION

This application claims priority to U.S. Provisional Application Ser. No. 60/225,665, filed Aug. 16, 2000.

BACKGROUND OF THE INVENTION

1. Field of the Invention

The present invention relates to stilbenoids that exhibit hypoglycemic and/or antidiabetic activity in mammals. Provided herein are processes for obtaining such stilbenoids, particularly from *Cajanus cajun*; compositions comprising the stilbenoids and methods for their use in treating diabetes mellitus and lowering blood glucose.

2. Related Art

Uses of Cajanus SPP

Plants of Cajanus spp. (Leguminoseae), particularly *C. cajun*, also known as pigon pea or redgram, are herbaceous members of the family Leguminoseae that grows widely throughout Africa, Asia and South and Central America. Cajanus spp. have been used in traditional medicine to treat stomach aches for women suspected of being pregnant, wounds and scalds, toothache, gonorrhoea, bad vision and heart diseases (Hedberg, H, et al., J Ethnopharmacol, 9 (2/3), 237–260 (1983).

In addition to its use by traditional healers, these plants may also be included in the normal diet as a food plant. Canjanus spp, for example, are consumed by people in India. To that end, studies have reported redgram and blackgram consumption's effect on blood glucose levels and glucose tolerance. (Srinivasan, M., Lancet 1957, 317 (1957)).

Extracts of *Cajanus cajan* have been reported to show hyypoglycemic activity. Dhar reported a 50% ethanolic extract of *Cajanus cajan* as exhibiting hypoglycemic activity. Dhar, M. L., et al., Indian J. Exp. Biol., 6, 232 (1968).

While extracts of the genus Cajanus have been used medicinally, such use is not without potential drawbacks. First, in addition to containing one or more compounds having a "desired" biological activity, plant materials often contain a myriad of naturally-occurring organic compounds among which one or more can elicit a physiological or pharmacological response that contraindicate use for the desired activity. Secondly, when administered in the form of a plant extract, the actual dosage of the unknown active compound(s) is impossible to regulate, which can result in an ineffective amount, i.e, too low a concentration, or a toxic amount, too high a concentration, of active compound administered.

Thus, there remains a need for an isolated or a purified, hypoglycemically active compound, compositions comprising therapeutically effective amounts of such a compound and methods for their use.

Compounds Isolated from Cajanus SPP

Stilbenoids

The term stilbenoid refers to stilbenes, bibenzyls and phenyldihydroisocoumarins together with a number of nitrogen free phenathrenols, which are thought to be products of the same metabolic pathway that leads to stilbenes. See generally Gorham, J., *Progress in Phytochemistry*, Vol. 6, Reinhold, et al., eds, Pergamon press, New York, 1980, pp 203–252. Stilbenes (dihydrostilbenes) generally have the basic two stereoisomeric forms, a trans- and a cis-skeleton:

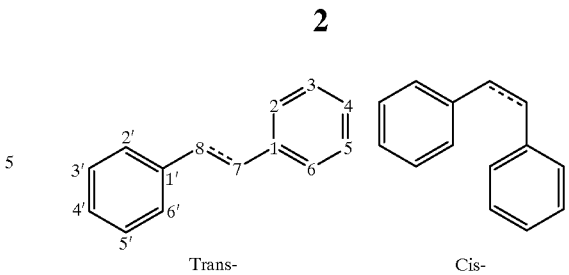

Generally, naturally occurring stilbenes and bibenzyls are hydroxy and/or methoxy substituted at the 3,3',4,4',5, and 5' positions. Some naturally occuring stilbenes and bibenzyls include pinosylvin (3,5-dihydroxy stilbene), piceatannol (3,3',4,5'-tetrahydroxlystilbene), piceid (3,4',5-trihydroxystilbene-3-O-β-D-glucopyranoside) and resveratrol (3,4'5-trihydroxystilbene). Mono- (3-hydroxy-5-methoxystilbene) and di-methyl (3,5-dimethoxystilbene) ethers of trans-pinosylvin and their respective dihydro-derivatives have been reported isolated from the heartwood of *Pinus armandi*, *P. morrisonicola*, and *P. parviflorai*. Fang, J-M, et al. Phytochemistry 27(5): 1395–1397 (1988).

Stilbenoids may also be prenylated or homogeranylated at the ortho (C-2 or C-6) or para (C-4) positions. Longistylines A (3-hydroxy-5-methoxy-4-(3-methyl-2-butenyl)stilbene), B (3,5-dihydroxy-2,4-di(3-methyl-2-butenyl)stilbene), C (3-hydroxy-5-methoxy-2-(3-methyl-2-butenyl)stilbene, and D (3,5-dihydroxy-2,6-di(3-methyl-2-butenyl)stilbene) were isolated from the bark and root of *Lonchocarpus longistylus*. Monache, F. D., et al. (Lloydia 40(2), 201–208 (1977)). 4-isopentenylresveratrol (3,4',5-trihydroxy-4-(3-methyl-2-butenyl)stilbene) was isolated from *Arachis hypogea* (Keen, N. T., et al., Phytochemistry 15, 1794 (1976)). A prenylated pinosylvin dimethyl ether (3,5-dimethoxy-4-(3-methyl-2-butenyl)stilbene) was isolated from *Derris rariflora* (Braz Filho, R., et al., Phytochemistry 14, 261 (1975a)) and *D.floribunda* (Braz Filho, R., et al., Phytochemistry 14, 1454 (1975b)). A prenylated resveratrol trimethyl ether (3,4',5-trimethoxy-4-(3-methyl-2-butenyl)stilbene) was also reported isolated from *D. floribunda* (Braz Filho, R., et al., 1975b). Chlorophorin (4-homogeranyl-2,3',4,5'-tetrahydoxysilbene) was isolated from *Chlorophora excelsa* (Grundon, M. F., et al., Nature (Lond.) 163, 154 (1949)). The occurrence in plants of isoprenice chains substituted stilbenes has also been reported by King and Grundo (J. Chem. Soc. 1950, 3547 (1950)); and Cooksey (Cooksey, C. J., et al., Phytochemistry 21(12), 2935 (1982)).

Prenylated bibenzyls have been isolated from Radula spp. Asakawa, Y, et al., reported the isolation of 3,5-dihydroxy-4-(3,7-dimethyl-2,6-octadienyl)-bibenzyl from *R. variabilis* (Phytochemistry 17, 2005 (1978a)) as well as the synthesis of mono and dimethyl ethers and corresponding tetrahydroderi-vatives. Asakawa reported the isolation from *Radula complanata* of bibenzyls prenylated or geranylated at 4 position. Asakawa, Y. et al., Phytochemistry 17, 2115 (1978b). Asakawa also reported the isolation of prenyl bibenzyls from *Radula kojana*. Asakawa, Y., et al., Phytochemistry 30(1), 219 (1991).

Four isoprenylated stilbene 2-carboxylic acid phytoalexins (3-hydroxy-5-methoxy-6-(3-methyl-2-butenyl)stilbene-2-carboxylic acid, 3-hydroxy-5-methoxy-4-(3-methyl-2-butenyl)stilbene-2-carboxylic acid, 3,5-dimethoxy-6-(3-methyl-2-butenyl)stilbene-2-carboxylic acid, and 3,5-dimethoxy-4-(3-methyl-2-butenyl)stilbene-2-carboxylic acid) were reported isolated from the leaves of *Canjanus cajan* challenged with *Botrytis cinierea* (Cooksey, C J, et al., Phytochemistry 21(12):2935–2938 (1982).

Various biological activities have been reported of the stilbenoids. For example, stilbenoids have been reported to show antioxidant activities [resveratrol] (A. Fauconneau, B., et al., Life Sci. 61(21):2103 (1997)); antifungal activity [3,3',4,5'-tetrahydroxystilbene](Inamori, Y., et al., Chem. Phar. Bull. 33(7):2904–09 (1985)); antiplatelet aggregation activity [resveratrol] (Chung, M-I, et al., Planta Med. 1992 58:274–275; and Kimura, Y., et al., Biochim.Biophys. Acta 1995 175, 275–278); coronary vasodilator activity (Inamori, Y., et al., Chem. Pharm. Bull. 35, 887–89 (1987); anti-leukemia activity (Mannila, E., Phytochemistry, 1003, 33, 813–816) and protein-tyrosine kinase inhibitory activity (Orsini, F., et al., J. Nat. Prods. 60, 1082–1087 (1997)).

Pterostilbene (3,4',5-trimethoxystilbene) isolated from *Pterocarpus marsupium* reportedly significantly decreased the plasma glucose level and body weights of of STZ-induced diabetic rats. Manickam, M., et al., J. Nat. Prods. 60, 609–610 (1996). Both the aqueous and alcoholic extracts of the heartwood of *Pterocarpus marsupium* were reported to produce a reduction in blood sugar level. Shah, D. S., Ind. J. Med. Res. 55(2), 166–168 (1967).

International patent application WO00/69430 by Nag et al. and published on Nov. 23, 2000 describes diphenylethylene compounds having the formula:

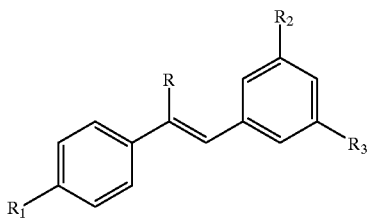

wherein,

R is hydrogen or —CO$_2$Z, Z is hydrogen or a cation;

R$_1$, R$_2$, and R$_3$ are each independently H, —OH, or OR$_4$, wherein R$_4$ is linear or branched alkyl of 1–12 carbon atoms; with the proviso that when R is hydrogen and R$_2$=R$_3$OMe, then R$_2$ is not OH.

These compounds are allegedly useful for the treatment of diabetes.

Citation or identification of any reference in the Background of this application shall not be construed as an admission that such reference is available as prior art to the present invention.

SUMMARY OF THE INVENTION

The present invention provides pharmaceutical compositions useful for treating hyperglycemia or reducing blood glucose levels comprising a pharmaceutically acceptable carrier and an effective amount of an isolated compound having the formula (I):

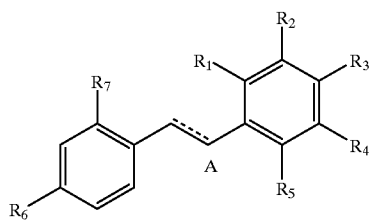

wherein,

A is selected from the group consisting of a single bond and a double bond in trans conformation, as noted by - - - - ;

R$_1$ is selected from the group consisting of H, OH, C$_{1-6}$alkoxy, COOH, and COOC$_{1-6}$alkyl;

R$_2$ is selected from the group consisting of H, OH, and C$_{1-10}$alkoxy;

R$_3$ is selected from the group consisting of H, C$_{1-10}$alkyl, C$_{2-10}$-alkenyl, C$_{2-10}$alkynyl, and C$_{1-8}$cycloalkyl;

R$_4$ is selected from the group consisting of H, OH, and C$_{1-10}$alkoxy;

R$_5$ are selected from the group consisting of H, C$_{1-10}$alkyl, C$_{2-10}$alkenyl, C$_{2-10}$alkynyl, and C$_{1-8}$cycloalkyl;

R$_6$ is selected from the group consisting of H, OH, C$_{1-6}$alkoxy, COOH, and COOC$_{1-6}$alkyl;

R$_7$ is selected from the group consisting of H, OH, C$_{1-6}$alkoxy, COOH, and COOC$_{1-6}$alkyl; and wherein at least one of R$_3$ and R$_5$ is selected from the group consisting of C$_{1-10}$alkyl, C$_{2-10}$alkenyl, C$_{2-10}$alkynyl; and C$_{1-8}$cycloalkyl;

or a pharmaceutically acceptable salt thereof.

The present invention also provides methods for treating hyperglycemia or reducing blood glucose levels to a mammal comprising administering to said mammal a hypoglycemically effective amount of an isolated or pure compound of formula (I). In particular embodiments, the invention provides methods of treatment for type I diabetes, type II diabetes, hyperthermia, trauma, sepsis, burns, severe head injury, cerebral-thrombosis, encephalitis, heat stroke, congenital metabolic glycogen storage diseases, and hyperglycemia that occurs as a adverse advent of anesthesia.

DETAILED DESCRIPTION OF THE INVENTION

Definitions

Figure 1:
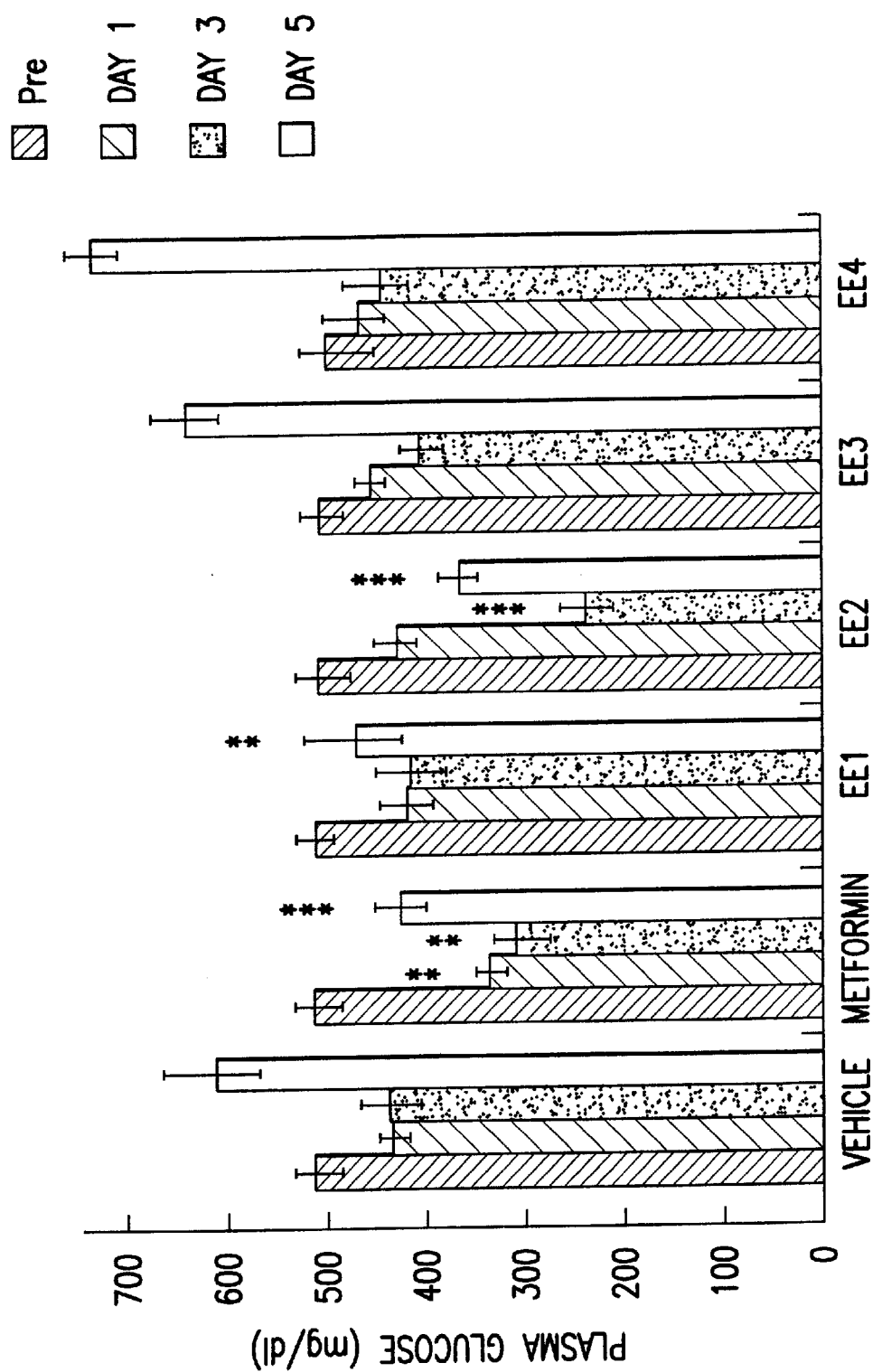
FIG. 1 is a bar graph showing the plasma glucose levels (mg/dL) of db/db mice treated with vehicle only, metformin, or 1000 mg/kg b.i.d. of enriched extracts of *Cajanus cajan* (EE1, EE2, EE3, or EE4) as described herein. The relevant extract or compound was administered to the animals at 0, 8, 24, 32, 48, 56, 72, 80, and 96 hours. Plasma glucose levels were measured at 0 (pre), 3 (Day 1), 51 (Day 3), and 99 (Day 5) hours post initial dosing. All data points n=8 *P<0.05; P<0.01; *P<0.001 (analysis of variance, one factor).

As used herein, the term "independently" or the equivalents thereof is employed to described an instance were two or more groups may be the same or different from each other and the occurrence of one group does not impact or influence the occurrence of the other group.

The term "alkyl" refers to a monovalent alkane (hydrocarbon) derived radical containing from 1 to 10 carbon atoms unless otherwise defined. It may be straight or branched. Preferred straight or branched alkyl groups include methyl, ethyl, propyl, isopropyl, butyl, 3-butyl, and t-butyl. Alkyl also includes a straight or branched alkyl group that contains or is interrupted by a cycloalkylene portion.

The term "cycloalkyl" refers to cyclic monovalent alkanes. Preferred cycloalkyl groups include cyclopentyl and cyclohexyl.

The term "alkenyl" refers to a hydrocarbon radical straight or branched containing from 2 to 10 carbon atoms and at least one carbon to carbon double bond. Preferably one carbon to carbon double bond is present, and up to four non-aromatic (non-resonating) carbon-carbon double bonds may be present. Preferred alkenyl groups include ethenyl, propenyl, butenyl and geranyl.

The term "alkynyl" refers to a hydrocarbon radical straight or branched containing from 2 to 10 carbon atoms and at least one carbon to carbon triple bond. Up to three carbon-carbon triple bonds may be present. Preferred alkynyl groups include ethynyl, propynyl and butynyl.

The term "alkoxy" represents an alkyl group of indicated carbon atoms attached through an oxygen linkage.

The present invention provides pharmaceutical compositions useful for treating hyperglycemia or reducing blood glucose levels comprising a pharmaceutically acceptable carrier and an effective amount of an isolated compound having the formula (I):

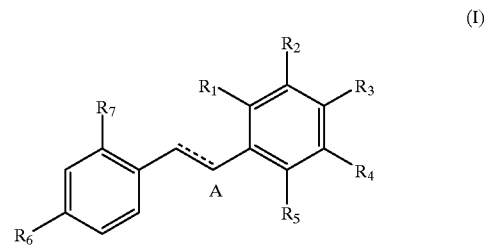

(I)

wherein,
A is selected from the group consisting of a single bond and a double bond in trans conformation;
$R_1$ is selected from the group consisting of H, OH, $C_{1-6}$alkoxy, COOH, and COOC$_{1-6}$alkyl;
$R_2$ is selected from the group consisting of H, OH, and $C_{1-10}$alkoxy;
$R_3$ is selected from the group consisting of H, $C_{1-10}$alkyl, $C_{2-10}$alkenyl, $C_{2-10}$alkynyl, and $C_{1-8}$cycloalkyl;
$R_4$ is selected from the group consisting of H, OH, and $C_{1-10}$alkoxy;
$R_5$ are selected from the group consisting of H, $C_{1-10}$alkyl, $C_{2-10}$alkenyl, $C_{2-10}$alkynyl, and $C_{1-8}$cycloalkyl;
$R_6$ is selected from the group consisting of H, OH, $C_{1-6}$alkoxy, COOH, and COOC$_{1-6}$alkyl;
$R_7$ is selected from the group consisting of H, OH, $C_{1-6}$alkoxy, COOH, and COOC$_{1-6}$alkyl; and
wherein at least one of $R_3$ and $R_5$ is selected from the group consisting of $C_{1-10}$alkyl, $C_{2-10}$alkenyl, $C_{2-10}$alkynyl; and $C_{1-8}$cycloalkyl;
or a pharmaceutically acceptable salt thereof.

In one embodiment of the present invention are pharmaceutical compositions and methods of treatment comprising a hypoglycemically effective amount of a compound having the formula (II):

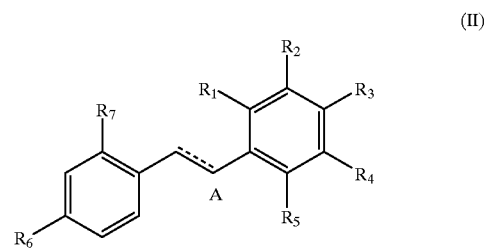

(II)

wherein,
A is selected from the group consisting of a single bond and a double bond in trans conformation;
$R_1$ is selected from the group consisting of H and —COOH;
$R_2$ is selected from the group consisting of H, OH and $C_{1-2}$alkoxy;
$R_3$ is selected from the group consisting of H, 3-methyl-2-butenyl, 3-methylbutyl, 3,7-dimethyl-2,6-octadienyl, and 3,7-dimethyloctadyl, R$_4$ is selected from the group consisting of H, OH and C$_{1-2}$alkoxy;

R$_5$ are selected from the group consisting of H, 3-methyl-2-butenyl, 3-methylbutyl, 3,7-dimethyl-2,6-octadienyl, and 3,7-dimethyloctadyl, R$_6$ is selected from the group consisting of H, OH, and C$_{1-2}$alkoxy; and R$_7$ is selected from the group consisting of H, OH and C$_{1-2}$alkoxy;

wherein at least one of R$_3$ and R$_5$ is selected from the group consisting of 3-methyl-2-butenyl, 3-methylbutyl, 3,7-dimethyl-2,6-octadienyl, and 3,7-dimethyloctadyl;

or a pharmaceutically acceptable salt thereof.

In a second embodiment of the present invention are pharmaceutical compositions and methods of treatment comprising a hypoglycemically effective amount of a compound having the formula (III):

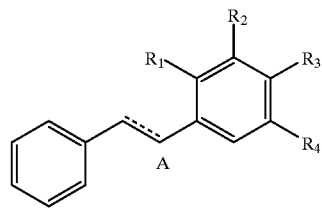

(III)

wherein:
A is selected from the group consisting of a single bond and a double bond in trans conformation;

R$_1$ is selected from the group consisting of H and COOH;

R$_2$ is selected from the group consisting of H, OH, and C$_{1-2}$alkoxy;

R$_3$ is selected from the group consisting of —CH$_2$CH═C(CH$_3$)$_2$ and —CH$_2$CH$_2$CH(CH$_3$)$_2$; and R$_4$ is C$_{1-2}$alkoxy;

or a pharmaceutically acceptable salt thereof.

In a third embodiment of the present invention are pharmaceutical compositions and methods of treatment comprising a hypoglycemically effective amount of a compound having the formula (IV):

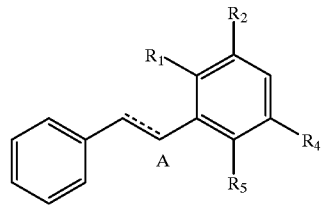

(IV)

A is selected from the group consisting of a single bond and a double bond in trans conformation;

R$_1$ is selected from the group consisting of H and COOH;

R$_2$ is selected from the group consisting of H, OH, and C$_{1-2}$alkoxy;

R$_4$ is C$_{1-2}$alkoxy; and

R$_5$ is selected from the group consisting of —CH$_2$CH═C(CH$_3$)$_2$ and —CH$_2$CH$_2$CH(CH$_3$)$_2$;

or a pharmaceutically acceptable salt thereof.

Preferred stilbenoid compounds of formula (I) are selected from the group consisting of:

Longistyline C (Cmd.A);
Longistyline A (Cmd.C);
longistyline A-6-carboxylic acid (Cmd.D);
7,8-dihydrolongistyline C (Cmd.E);
7,8,2",3"-tetrahydrolongistyline C (Cmd.F);
7,8,2",3"-tetrahydrolongistyline A-6-carboxylic acid (Cmd.H);
3-hydroxy-4isoprenyl-5-methoxystilbene-2-carboxylic acid;
3-hydroxy-4-(3-methylbutyl)-5-methoxy-7,8-dihydrostilbene-2-carboxylic acid;
4-isopentenylresveratrol (3,4',5-trihydroxy-4-(3-methyl-2-butenyl)stilbene; (Cmd.AA);
3,5-dimethoxy-4-(3-methyl-2-butenyl)stilbene (Cmd.AB);
3,4',5-trimethoxy-4-(3-methyl-2-butenyl)stilbene 27 (Cmd.AC);
chlorophorin (Cmd.AD);
3,5-dimethoxy-4-(3-methyl-2-butenyl)bibenzene (Cmd.AE);
3,5-dihydroxy-4-(3-methyl-2-butenyl)bibenzene (Cmd.AF);
3,5-dihydroxy-4-(3-methyl-2-butenyl)bibenzyl-2-carboxylic acid (Cmd.AG);
3-hydroxy-5-methoxy-4-(3-methyl-2-butenyl)bibenzene (Cmd.AH);
5-hydroxy-3-methoxy-4-(3-methyl-2-butenyl)bibenzene (Cmd.AI);
3,5-dihydroxy-2-(3-methyl-2-butenyl)bibenzene (Cmd.AJ);
3-hydroxy-5-methoxy-2-(3-methyl-2-butenyl)bibenzene (Cmd.AK);
5-hydroxy-3-methoxy-2-(3-methyl-2-butenyl)bibenzene (Cmd.AL);
3,5-dihydroxy-4-(3,7-dimethyl-2,6-octadienyl)-bibenzene (Cmd.AM);
3,5-dimethoxy-4-(3,7-dimethyl-2,6-octadienyl)-bibenzene(Cmd.AN);
3,5-diacetyl-4-(3,7-dimethyl-2,6-octadienyl)-bibenzene (Cmd.AO);
3,4', 5-trihydroxy4-(3,7-dimethyl-2,6-octadienyl)-bibenzene (Cmd.AP);
3,5-dihydroxy-4-(3,7-dimethyloctyl)bibenzene (Cmd.AQ);
3,5-dimethoxy-4-(3,7-dimethyloctyl)bibenzene (Cmd.AR);
2-geranyl-3,5-dihydroxybibenzene (Cmd.AS);
2-geranyl-3,5-dimethoxybibenzene (Cmd.AT);
2-geranyl-3-hydroxy-5-methoxybibenzene (Cmd.AU); and
3-methoxy-4'-hydroxy-4-(3-methyl-2-butenyl)bibenzene (Cmd.AV).

Pharmaceutical compositions contain a pharmaceutically acceptable carrier or vehicle, a hypoglycemically effective amount of a compound of formula (I) and optionally another hypoglycemic, anti-diabetic, or anti-lipidemic agent useful for lowering blood glucose or lowering fatty acids.

Specific Embodiments of the Present Invention

The following compounds illustrate the structure and nomenclature of the compounds of Formula (I) and other compounds described herein.

3-hydroxy-5-methoxy-4-(3-methyl-2-butenyl)stilbene;
3-methoxy-4-(3-methyl-2-butenyl)-5-(trans-styryl)phenol.

Compound A

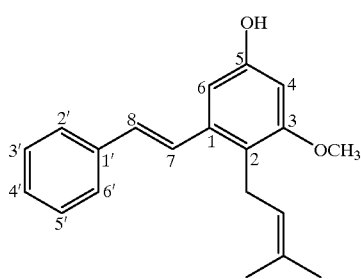

Compound A may also be known as Longistyline C; 3-hydroxy-5-methoxy-6-isoprenylstilbene; 5-hydroxy-3-methoxy-2-isoprenylstilbene; 5-hydroxy-3-methoxy-2-(3-methyl-2-butenyl)stilbene and 3-methoxy-4-(3-methyl-2-butenyl)-5-(trans-styryl)phenol.

Compound B

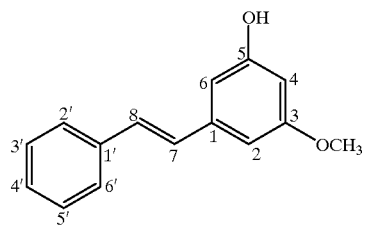

Compound B may also be known as pinosylvin monomethyl ether; 3-hydroxy-5-methoxystilbene; and 3-methoxy-5-(trans-styryl)phenol.

Compound C

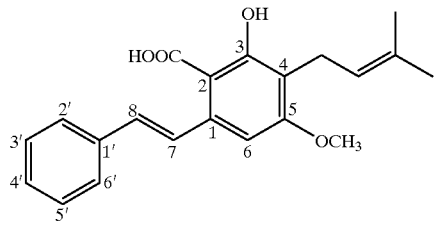

Compound C may also be known as Longistyline A-6-carboxylic acid; Longistyline A-2-carboxylic acid; 3-hydroxy-4-isoprenyl-5-methoxystilbene-2-carboxylic acid; 3-hydroxy-4-(3-methyl-2-butenyl)-5-methoxystilbene-2-carboxylic acid; 2-hydroxy-4-methoxy-3-(3-methyl-2-butenyl)-6-(trans-styryl)benzoic acid.

Compound D

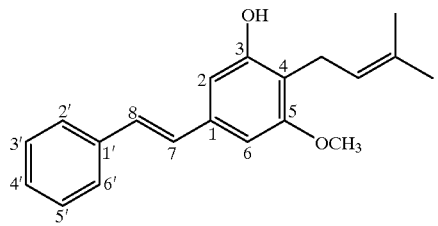

Compound D (Compound 3) may also be known as Longistyline A; 3-hydroxy-4-isoprenyl-5-methoxystilbene;

Compound E

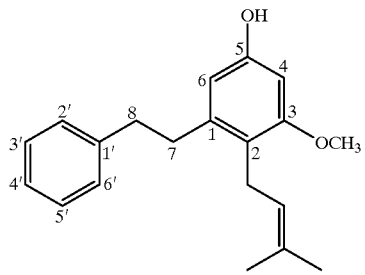

Compound E (compound 7, A) may also be known as 7,8-dihydrolongistyline C; 5-hydroxy-2-(3-methyl-2-butenyl)-3-methoxybibenzene; 3-hydroxy-6-isoprenyl-5-methoxybibenzene; 5-hydroxy-2-isoprenyl-3-methoxybibenzene; 1-(3-methoxy-6-(3-methyl-2-butenyl))benzyl-4-benzylethane.

Compound F

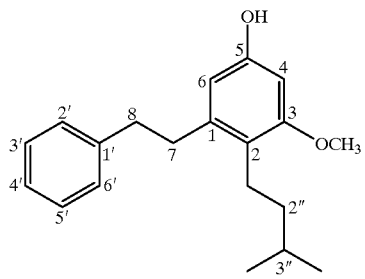

Compound F (Compound 6, IA) may also be known as 7,8,2",3"-tetrahydrolongistyline C; 5-hydroxy-3-methoxy-2-(3-methylbutyl)bibenzene; 5-hydroxy-3-methoxy-2-isopentenyl-bibenzene; 3-hydroxy-6-isopentenyl-5-methoxybibenzene; 3-hydroxy-5-methoxy-2-(3-methylbutyl) bibenzene; 1-(5-hydroxy-3-methoxy-2-(3-methylbutyl)benzyl)-4-benzylethane.

Compound G

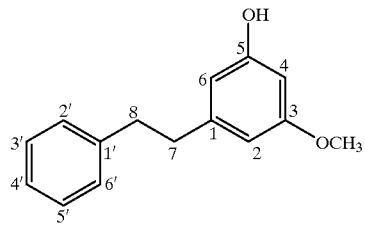

Compound G (Compound 5, IA) may also be known as 7,8-dihydropinosylvin monomethyl ether; 5-hydroxy-3-methoxybibenzene; 3-hydroxy-5-methoxybibenzene; and 3-methoxy-5-(trans-styryl)phenol; 1-(3-methoxy-5-methoxybenzyl)-4-benzylethane.

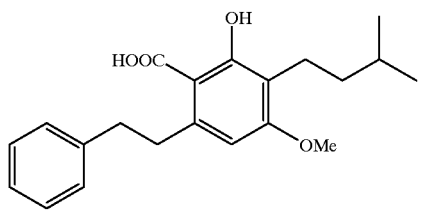

Compound H

Compound H (Compound 8) may also be known as 7,8,2",3"-tetrahydrolongistyline A-2-carboxylic acid; 3-hydroxy-4-isopentenyl-5-methoxybibenzyl-2-carboxylic acid; 3-hydroxy-5-methoxy-4-(3-methylbutyl)bibenzyl-2-carboxylic acid; 1-(3-hydroxy-5-methoxy-4-[3-methyl-2-butenyl])phenol-4-phenolethane.

The hypoglycemically active stilbenoids of formulae described herein can be isolated directly from Cajanus spp., preferably from *C. cajun*, or chemically synthesized and isolated from a reaction mixture. The hypoglycemically active stilbenoids of formulae described herein, e.g., Compounds A,B,C,E, and H can also be isolated directly from other species, e.g., *Lonchocarpus longistylus* (Compound A); *Pinus spp* (Compound B); *Lonchocarpus violaceus* (Jack) DC (*Lonchocarpus longistylus* Pittier) (Compound C); *Radula kojana* (Compound E); and *Pinus strobus* var. chiapensis (Compound G). The isolated hypoglycemically active stilbenoids of formulae described herein can be obtained in purified form, preferably in substantially purified form, via column chromatography, recrystallization or other means known to those skilled in the art. In an additional embodiment, the hypoglycemically active stilbenoids of formulae described herein can be obtained in a manner which results in an enriched extract or isolate having the desired stilbenoid level in a convenient dosage form. The hypoglycemically active stilbenoids of formulae described herein, e.g., Compounds AA–AV, can also be isolated directly from other plants, including, for example, *Lonchocarpus violaceus* (Monache 1977); *Arachis hypogea* (Ingham, J. L., Phytochemistry 15, 1791); *Derris rariflora* (Braz Filho, R., et al., Phytochemistry 14, 261 (1975a)); *D.floribunda* (Braz Filho, R., et al, Phytochemistry 14, 1454 (1975b; *Chlorophora excelsa* (Grundon, M. F., Nature (lond.) 163, 564 (1949)); and *Radula complanata* and *R. kojana* (Asakawa, Y., et al., 1978(a), 1978(b), and (1991)) Keen, N. T., et al., Phytochemistry 15, 1794 (1976) as described more fully in the following paragraphs.

Processes for Isolating Hypoglycemically Active Stilbenoids

Compound A–H can be isolated from Cajanus spp., preferably *C. cajun* using the illustrative methods described below or other standard extraction and purification techniques known to those of ordinary skill in the art Compounds A–H can be isolated from other sources by techniques known to those of ordinary skill in the art. Compound A has previously been reported isolated from *Lonchocarpus violaceus* (Monache, et al., 1977) and from *Cajanus cajan* (Chung Ts'ao Yao, 1985, 18, 2). Compound B has been reported isolated from *Alnus sieboldiana* (Betulaceae) (Asakawa, Y., et al., Bull.Chem.Soc.Jpn 44, 2671 (1971) (1991)). Compound C was reported isolated from *Cajanus cajan* (Cooksey, C. J., et al., 1982). Compound D (longistyline A) has been reported isolated from *Lonchocarpus violaceus* Monache, et al. (1977). Compound E (dihydrolongistyline C) was reported isolated from *Radula kojana* (Asakawa, et al., Phytochemistry 30(1), 219–234 (1991); and Compound G has been previously reported isolated from *Pinus strobus* var. chiapensis (J. Braz. Chem. Soc. 1996, 7, 1996). Compounds F and H were prepared by hydrogenation of Compounds A and C respectively. Compounds AA–AP have been reported isolated by Asakawa 1978a, 1978b, 1991; Keen, N. T., et al., 1976; Braz Filho, R., et al., 1975a; and 1975b; Grundon, et al. 1949; and Monache, 1977. In addition, the Compounds A–H and AA–AV so obtained can be purified by chromatography, recrystallization or other purification methods known to those skilled in the art.

Isolation and Purification of Hypoglycemically Active Stilbenoids

Plant material from the natural source, for example Cajanus spp., preferably *C. cajun* (Leguminoseae), is initially extracted with a solvent to provide a crude extract containing the identified stilbenoids. By "plant material" is meant any part of the plant, such as bark, leaves, flowers, roots and stems. The plant material may optionally be shredded, ground, macerated, or otherwise treated prior to extraction. Alternatively, the plant material may already be in a powdered, shredded, ground, macerated, or comminuted state when used herein. Suitable extraction solvents include polar solvents, non-polar solvents, or mixtures thereof. Useful polar solvents include, but are not limited to, acetonitrile, methanol, ethanol, isopropanol, acetone, butanol, ethyl acetate, water and mixtures thereof. Useful non-polar solvents include, pentane, hexane, heptane, higher alkane and other hydrocarbon solvents, such as petroleum ether.

Preferably, the plant material is extracted with a polar solvent, so as to maximize the amount of stilbenoids that can be extracted from the plant material. More preferably, the plant material is washed with a mixture of polar solvent and water, wherein the ratio of water to polar solvent ranges from 1:99 to 99:1 volume/volume (v/v). Most preferably, the polar solvent is an organic alcohol, such as methanol, ethanol, isopropanol, butanol and the like. When the organic alcohol is ethanol, the ratio of water to organic alcohol is preferably about 5:95 to about 95:5 (v/v), more preferably from about 10:90 to about 30:70 (v/v) and most preferably about 20:80 (v/v).

Washing the plant material with solvent can be performed at a temperature of about room temperature to about the reflux temperature of the chosen solvent or solvent system, preferably at room temperature, for between about 2 hours and 72 hours, preferably for between about 24 hours, in order to maximize the amount of stilbenoids that can be isolated from the plant material.

The plant material may also be agitated, soaked-or otherwise exposed to the solvent to facilitate the extraction process. For example, the plant material can be mechanically mixed, sonicated, or otherwise agitated in the solvent by methods known by those skilled in the art.

The resulting crude extract can then filtered to remove undesired solid or waste plant materials, e.g., spent plant residue/materials therefrom and to afford a crude filtrate containing the stilbenoids. Suitable filtering methods include passing the crude extract through diatomaceous earth, e.g., diatomaceous earth sold under the trademark "CELITE™" by Fisher Scientific Inc. (Los Angeles, Calif.); or a fritted funnel. Centrifugation of solutions or diluted solutions of the crude extract can also be employed to remove undesired solid therefrom.

The crude filtrate is concentrated, preferably in vacuo, and the resulting residue further purified by being partitioned between two partitioning solvents, so as to enhance the yield and overall purity of the isolated stilbenoids. It is important that the partitioning solvents are immiscible in each other. Preferably, one of the partitioning solvents is a non-aqueous solvent such as toluene, diethyl ether, ethyl methyl acetate, chloroform, carbon tetrachloride, ethyl acetate, pentane, hexane, heptane, higher alkane (C<7) solvents, dichloromethane and other hydrocarbon solvents, such as petroleum ether. known by those skilled in the art to be immiscible in water or capable of dissolvating stilbenoids. The aqueous solvent should preferably be capable of dissolving impurities found in the plant material.

The organic phase, containing the stilbenoids, is separated, optionally combined, and then concentrated to dryness to afford a crude concentrate, which is enriched in stilbenoids. The previously described extraction and filtering steps can be repeated to increase the yield and overall purity of the isolated stilbenoids. The crude concentrate can be further purified by standard techniques known to those skilled in the art to ultimately afford isolated stilbenoids. Exemplary purification techniques include recrystallization and chromatography. Preferably, the crude concentrate is purified using liquid chromatography, for example high performance liquid chromatography, vacuum flash chromatography and adsorpton chromatography.

Various resin types can be utilized to achieve the desired chromatographic effect. For example, in order to remove polar impurities therefrom, the crude concentrate can be passed through an adsorption resin (HP-20 grade resin sold by Mitsubishi-Kasei, located in White Plains, N.Y.; C-18 (octadecyl) resin sold by J. T. Baker of Phillipsburg, N.J., or Supelco of Bellefonte, Pa.; or other silica gel) to selectively retain or pass the stilbenoids according to polarity. Size, molecular weight, or cellulosic characteristics of the desired resin material may be used to separate the stilbenoids by selective use of molecular exclusion or cellulose based resins.

An appropriate gradient solution is used to wash and separate the stilbenoids from the crude concentrate on the column filled with the desired resin. A suitable gradient may include an initial solvent wash followed by an elution solvent. Suitable elution solvents contain a high percentage of acetonitrile (ACN), methanol, acetone, dichloromethane, ether/hexane or any other organic solvent or mixtures thereof that can release stilbenoids from the resin material, and into an enriched fraction. The enriched fraction will be stilbenoids, or mixtures thereof. The elution solvent can contain up to 50% water, so as to adjust or optimize the polarity thereof. The type of elution solvent can depend upon the the type of resin used. For example, for HP-20 resin equilibrated in methanol, the elution solvent can be dichloromethane; for C-18 resin equilibrated in 70% ACN/30% water (v/v), a gradient of increasing acetonitrile concentration is appropriate; or for silica gel resin equilibrated in hexane, the elution solvent can be a gradient of increasing ether in a ether/hexane concentration solution.

High performance liquid chromatography (HPLC), thin layer chromatography (TLC) and nuclear magnetic resonance (NMR) analysis can be used to determine which of the eluting: fractions is an enriched fraction, and which enriched fractions contain the desired stilbenoids. Optionally, different eluting fractions can be combined and subjected to the TLC and NMR analyses described above. The enriched fractions can optionally be repurified using either the same or a different eluent system.

The resulting fractions containing the stilbenoids are concentrated, optionally in vacuo. The fractions containing the stilbenoids from the chromatography methods described above can be combined and further purified by successive iterations of the above, or by recrystallization or other types of chromatography. Optionally, successive recrystallization or chromatography purifications may be performed to obtain purified stilbenoids.

Using the above purification techniques, the isolated stilbenoids can be purified or substantially purified. By "substantially purified" is meant that the stilbenoids of formulae described herein have a degree of purity of at least about 95%. By "purified" is meant that the stilbenoids of formulae described herein have a degree of purity of at least about 97%.

Organic Synthesis of Hypoglycemically Active Stilbenoids

There are two main methods for synthesizing stilbenoids, the earliest being variations on the Perkin condensation of a phenylacetic acid with a benzaldehyde to form a stilbene-α-carboxylic acid, followed by decarboxylation. Funk, C, et al, Chem. Ber., 38, 939 (1905); Buckles, R. E., et al., J. Am. Chem. Soc. 73, 4972 (1951); and Letcher, R. M., Phytochemistry 12, 2789 (1973). Moreover, the Wittig reaction between a benzyltriphenylphos-phonium chloride or a diethylbenzylphosphonate and a benzaldehyde has been used to give a higher yield of a predominantly trans-stilbene. Gorham, J., Phytochemistry, 16, 249 (1977); Wheeler, O. H., et al., J. Org. Chem. 30, 1473 (1965). Bibenzyls are also readily prepared from stilbenes by catalytic hydrogenation with hydrogen in the presence of palladium on carbon.

The compounds of formulae described herein may also be semi-synthesized from other isolated stilbenoids. 3-hydroxy-5-methoxy-4-isoprenylstilbene-2-carboxyolic acid (Compound C) and 3-hydroxy-5-methoxy-6-isoprenylstilbene-2-carboxylic acid were reported isolated from Cajanus cajun (Cooksey, C. J., et al., (1982)). Methylation of these compounds with diazomethane gave 3,5-dimethoxy-6-isoprenylstilbene-2-carboxylic acid and 3,5-dimethoxy-4-isoprenylstilbene-2-carboxylic acid, respectively. Cooksey, C J, et al. (1982).

Prenylated bibenzyls have been semi-synthesized from pinosylvin and pinosylvin mono-methyl ether by hydrogenation, treatment with sodium methoxide in methanol and then 2,2-dimethylallylbromide to give 3-hydroxy-5-methoxy-2-(3-methyl-2-butenyl)bibenzene, 3-hydroxy-5-methoxy-4-(3-methyl-2-butenyl)bibenzene, and 3-hydroxy-2,4-di(3-methyl-2-butenyl)bibenzene. Asakawa also described synthesizing 2-geranyl-3-hydroxy-5-methoxybibenzene, 4-geranyl-3-hydroxy-5-methoxybibenzene, 2,4-digeranyl-3-hydroxy-5-methoxybibenzene, 2-geranyl-3,5-dihydroxybibenzene; and 2-geranyl-3,5-dimethoxybibenzene. Asakawa (1991).

Hypoglycemically active stilbenoids may also be synthesized in vivo by a phenylpropanoid-polymalonate pathway. Pryce, R. J., Phytochemistry, 10, 2679 (1971).

Once the hypoglycemically active stilbenoids of formulae described herein have been synthesized, they can be purified or substantially purified, using conventional chromatography, recrystallization or other purification techniques known to those skilled in the art.

Derivatives of Hypoglycemically Active Stilbenoids

Also included within the scope of the present invention are ether and acetate derivatives of stilbenoids that are useful for lowering blood glucose. For example, the carboxylic acid groups of the stilbenoid-2-carboxylic acids can be methylated with $CH_2N_2$ and ether to produce the methyl ether thereof. The hydroxy groups of the stilbenoids can also be methylated by adding MeI in the presence of $K_2CO_3$ to a compound in $Me_2CO$ to give mono- and di-methyl ethers. (Asakawa, 1991).

In addition, the hydroxyl groups of these stilbenoids can be acetylated by methods well known to those skilled in the art, for example, using acetyl chloride (Greene, *Protective Groups in Organic Synthesis* 101, (1981)).

It is to be pointed out that any hydroxyl groups not so methylated or acetylated can participate in the formation of those pharmaceutically acceptable salts of stilbenoids described above.

Pharmaceutical Compositions of Hypoglycemically Active Stilbenoids

The stilbenoids of formulae described herein may be compounded, for example with a pharmaceutically acceptable carrier for solid compositions such as tablets, pellets or capsules; capsules containing liquids; suppositories; solutions; emulsions; suspensions or any other form suitable for use. Suitable carriers include, for example, sterile water, sterile physiological saline, gum acacia, gelatin, starch paste, talc, keratin, colloidal silica, urea and the like. In addition, auxiliary, stabilizing, thickening, lubricating and coloring agents may be used. The stilbenoids of formulae described herein are present in the compositions in an amount sufficient to produce a desired effect upon diabetes, blood glucose levels; or hyperglycemia.

Compositions for oral administration may be in the form of tablets, troches, lozenges, aqueous or oily suspensions, granules or powders, emulsions, capsules, syrups or elixirs. Orally administered compositions may contain one or more agents, such, as sweetening agents such as fructose, aspartame or saccharin; flavoring agents such as peppermint, oil of wintergreen, or cherry, coloring agents and preserving agents to provide a pharmaceutically palatable preparation. Moreover, compositions in tablet form may be coated to delay disintegration and absorption in the gastrointestinal tract thereby providing a sustained action over an extended period of time. Selectively permeable membranes surrounding an osmotically active driving compound are also suitable orally administered compositions. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monosterate or glycerol stearate may also be used.

Aqueous suspensions containing the stilbenoids of formulae described herein may also contain one or more preservatives, such as, for example, ethyl or n-propyl-p-hydroxy-benzoate, one or more coloring agents, flavoring agents or sweetening agents.

Dietary Supplements Containing Hypoglycemically Active Stilbenoids

The stilbenoids of formulae described herein can be used in the form of a food additive, food supplement, dietary supplement for example, in solid, semisolid or liquid form, which contains at least one of the stilbenoids of formulae described herein, preferably longistyline C (Compound A); longistyline A-6-carboxylic acid (Compound D); longistyline A (Compound C); 7,8-dihydrolongistyline C (Compound E); 7,8,2",3"-tetrahydrolongistyline C (Compound F); and 7,8,2",3"-tetrahydrolongi-styline A-6-carboxylic acid (Compound H), including their therapeutically active salts, as a bioactive component. When incorporated into foodstuffs, the hypoglycemically active stilbenoid may be used as an isolated compound or may be contained in an enriched fraction of plant extract.

The compounds of the present invention may be incorporated into foodstuffs alone or in combination with another antidiabetic, antihyperglycemic (blood glucose lowering), or anti-lipidemic compound, in admixture with a carrier or an excipient suitable for oral administration.

Compositions for oral administration may be in the form of foodstuffs comprising the compositions of this invention.

Any conventional food processing technique may be used to achieve a product comprising the effective amount of the stilbenoid compound of formula (I). There is much information on the art and technology of the various conventional food processing techniques and their practices in both the pet food and food industries, and it is accordingly assumed that the general principals of these techniques are understood by the person skilled in the art.

With the addition of a stilbenoid to a carrier material, the method of assimilating the stilbenoid compound is not limited to simple baking or dehydration, but may also include such techniques as extrusion processing, coextruding, and canning. Additionally, the process by which granola bars and food bars are prepared may be used to prepare the present foodstuffs. Thus, various types of food products may be produced in the practice of the invention in addition to powder ingredients for finished foods. For example, foodstuffs produced in the practice of the invention include dry pet foods that serve as a complete nutritional diet for pets, as well as biscuits and treats for pets. Additionally, the present foodstuffs may be formed into cereals, snacks, and nutrition bars for humans. Regardless of the method by which the present foodstuffs are prepared or the components therein, it is preferred that the resulting foodstuffs will provide a stilbenoid concentration of at least about 0.1 gram per dietary unit.

In the practice of the invention, the carrier material is contemplated to be a dry material of proteinaceous or farinaceous character. Nonexclusive examples of suitable carrier materials include: dried bakery product, the flours of wheat, rice, oat, corn, and soy; the brans of wheat, rice, oat, and corn; wheat middlings; whole ground wheat, corn gluten meal, whole ground corn, soybean meal, barley, sorghum, meat and bone meals, poultry meal, fish meal, dry dog food, and the like of the various materials that typify conventional commercial and premium pet food products.

The foodstuff produced in the practice of the invention may take any form that is edible by humans or pets, including a complete and balanced pet food; a dry or semi-dry product that is an additive for pet food or human food; or granola-type bars, nutrition bars or other snacks for humans. Specifically, if the foodstuff comprises a stilbenoid of formula (I), it is contemplated that it will be employed as an ingredient to be incorporated into another foodstuff. Toward that end, the stilbenoid can be in the form of a powder or fine meal that may then serve as an ingredient to other foods. Additional examples of foodstuffs contemplated for human consumption that may include, as an ingredient, stilbenoids processed in accordance with the invention include fillings or puddings (similar to gelatins and JELLO products), as well as performance foods in liquid gel form and canned soups.

Methods for Use of the Hypoglycemically Active Stilbenoids

Due to the activity of the stilbenoids of the present invention, the stilbenoids of formulae described herein, including longistyline C (Compound A); longistyline A-6-carboxylic acid (Compound D); longistyline A (Compound C); 7,8-dihydrolongistyline C (Compound E); 7,8,2",3"-tetrahydrolongistyline C (Compound F); and 7,8,2",3"-tetrahydrolongistyline A-6-carboxylic acid (Compound H) or pharmaceutically acceptable salts thereof are advantageously useful pharmaceutical compositions and dietary supplements. Such compositions and dietary supplements may be used to treat mammals suffering from hyperglycemia or diabetes or in veterinary and human medicine for therapeutic treatment of complications that result in hyperglycemia. In one embodiment of the present invention the pharmaceutical compositions or dietary supplements are used to lower blood glucose in mammals with type I or type II diabetes. Additionally, the stilbenoids of formulae described herein can be advantageously used as hypoglycemic agents to reduce blood glucose in situations of acute stress such as experienced by animals or patients with hyperthermia, trauma, sepsis, burns or those undergoing general anesthesia. Hyperglycemia sometimes associated with severe head injury, cerebral-thrombosis, encephalitis and heat stroke can also be therapeutically treated with the stilbenoids of formulae described herein. Additionally, the stilbenoids of formulae described herein are useful as hypoglycemic agents for rare congenital metabolic glycogen storage disease associated with hyperglycemia. The stilbenoids of formulae described herein used in the methods described herein are particularly suited to control hyperglycemia in patients whose blood glucose cannot be controlled by diet alone. Furthermore, the stilbenoids of formulae described herein are capable of lowering blood glucose levels without an accompanying increase in urine glucose levels.

When administered to a mammal for veterinary use or to a human for clinical use, the stilbenoids of formulae described herein are administered in isolated form. By "isolated" is meant that the stilbenoids of formulae described herein are separated from other components of either (a) a natural source such as a plant or cell culture, or (b) a synthetic organic chemical reaction mixture. Preferably, via conventional techniques, the stilbenoids of formulae described herein are substantially purified, preferably purified.

When administered to a mammal for veterinary use or to a human for clinical use, the stilbenoids of formulae described herein can be used alone or in combination with any physiologically acceptable carrier or excipient suitable for enteral or parenteral administration. Where used for parenteral administration, the physiologically acceptable carrier must be sterile and suitable for in vivo use in a human, or for use in a veterinary clinical situation.

The compositions of this invention may be administered by a variety of methods including orally, intramuscularly, intravenously, subcutaneously, transdermally, rectally or by inhalation. While the preferred mode of administration is through the oral mode, the precise mode of administration is left to the discretion of the practitioner. They are advantageously effective when administered orally.

This invention comprises the use of a stilbenoid, preferably in isolated or purified form administered at a dose of about 1 to about 1,000 mg per kg of body weight per day, preferably from about 2 to about 500 mg per kg of body weight per day, more preferably about 5 to about 350 mg per kg of body weight per day, still more preferably about 50 to about 350 mg per kg of body weight per day. In still a further embodiment, the invention comprises the use of a stilbenoid of formulae described herein at a dose of about 5 to about 350 mg/kg body weight/day of compound to be utilized in an amount which results in the compositions exhibiting a therapeutically effective hypoglycemic, antihyperglycemic or antidiabetic activity. The dosage of the present compositions for treatment or prevention of hyperglycemia or diabetes or for reducing blood glucose levels, depends on the route and frequency of administration was well as the age, weight and physical condition of the patient. Generally the daily dosage is in the range of about 1 to about 1,000 mg per kg of body weight per day, preferably from about 2 to about 500 mg per kg of body weight per day, more preferably about 5 to about 350 mg per kg of body weight per day, still more preferably about 50 to about 350 mg per kg of body weight per day. Treatment can be repeated as needed, depending upon the dosage and need, for example, a dosage of about 62.5, 125 or 250 mg/kg body weight/day of patient animal can be administered in dividing doses to prevent or treat diabetes or hyperglycemia or to lower blood glucose. Treatment can be continued, for example, reduced to the desired until the blood glucose level is level or to be maintained at a desired level. The appropriate dosage of the compositions can be readily determined by the skilled medical practitioner.

For the treatment of diabetes, hyperglycemia effecting a lowering of blood glucose, a composition of present invention may be administered which contains a stilbenoid of formulae described herein or a pharmaceutically or the acceptable salt thereof as described above, together with another antidiabetic, antihyperglycemic or blood glucose lowering agent including, but not limited to insulin; a biguanide such as metformin or buformin; a sulfonylurea such as acetohexamide, chlorpropamide, tolazamide, tolbutamide, glyburide, glypizide or glyclazide; a PPARγagonist including but not limited to the thiazolidinediones (such as troglitazone); an α-glucosidase inhibitor such as acarbose or miglitol; a Pradrenoceptor agonist such as PL-316, 243, etc., cholestyramine, clofibrate, colestipol, fluvastatin, gemfibrozil, lovastatin, niacin, pravastatin, probucol, psyllium hydrophilic muccilloid, simvastatin, and sodium dichloroacetate. Alternatively, the compositions comprising a hypoglycemically active stilbenoid or a pharmaceutically acceptable salt thereof can be administered in combination with, prior to, concurrent with or subsequent to the administration of another antidiabetic, antihyperglycemic, or anti-lipidemic agent as described supra.

Although the present inventors do not wish to be limited to any particular mechanism of action to explain the hypoglycemic activity of the stilbenoids of formulae described herein, it is envisaged that they may advantageously be useful for treatment of both insulin-dependent or type I diabetes (formerly termed juvenile-onset or ketosis prone diabetes) and non-insulin-dependent or type II diabetes (formerly termed adult-onset, maturity onset or nonketotic diabetes). The stilbenoids of formulae described herein can optionally be administered in an effective amount as pharmaceutically acceptable carboxylate or phenolate salts using counter ions such as sodium, potassium, lithium, calcium, magnesium, zinc and iron.

The following examples are set forth to assist in understanding the invention and should not, of course, be construed as specifically limiting the invention described and claimed herein. Such variations of the inventions which would be within the purview of those in the art, including the substitution of all equivalents now known or later developed, including changes in formulation or minor changes in experimental design, are to be considered to fall within the scope of the invention incorporated herein.

EXAMPLES

Example Isolation and Characterization of Stilbenoid Compounds

Materials and Methods

Analytical high performance liquid chromatography (HPLC) was performed on a Hitachi Model D-6500 Chromatography Data Station equipped with a D-6000 interface, L-6200A pump, AS-2000 autosampler, L4500A diode array detector and a Sedex 55 light scattering detector connected in series, and a Primesphere C18 HC, 4×50 mm (5 μm) HPLC column. All chromatographic runs were performed at ambient temperature. HPLC grade solvents were used without further purification.

Nuclear magnetic resonance (NMR) spectra were recorded on a Varian Unity Plus 400 or a Varian Unity 400 spectrometer. NMR spectra of compounds were recorded in deuterated chloroform. One and two-dimensional NMR experiments, including $^1$H NMR, $^{13}$C NMR, Heteronuclear Multiple Quantum Correlation (HMQC), and Heteronuclear Multiple Bond Correlation (HMBC) provided molecular structure information. Mass spectra were recorded on a Kratos MS-50 in high resolution power electron impact scanning mode, 70 eV. Resolution was set to 2000 with a scanning rate of 10 sec/decay. Samples were ran on a temperature gradient from 50° to 300° C., increased at a rate of 50°/min. Infrared spectra were recorded on a Perkin-Elmer 1600 Series FTIR. Ultraviolet spectra were taken directly from the Hitachi diode-array UV detector on the HPLC system.

Isolation of Stilbene Compounds Using Solvent Extraction

Small Scale Extraction and Isolation

Ground Leaf material of *Cajanus cajan* (4.2 kg) was extracted with 50 L of 80% ethanol (EtOH) (80% ethanol:20% water v/v) by stirring mechanically at room temperature for 24 hours. The solution was then filtered through CELITE™ and the filtrate was evaporated to dryness under vacuum. The residue was subsequently dried in a vacuum oven overnight to give 521 g. This was partitioned between DCM (10 L) and H$_2$O (10 L). The DCM layer was passed through CELITE™ and evaporated to dryness under vacuum to give 225 g of material. From this, 30.0 g was adsorbed onto 37 g Si gel and added to an open column containing 180 g Si gel. The column was eluted with hexane and increasing percentages of ethyl acetate (EtOAc). A total of seven fractions were collected. Compounds B (0.59 g), Compound A (1.05 g) and Compound C (1.21 g) from fraction four were obtained by preparative HPLC separation (MeCN/H$_2$O gradient, 60 mL/min). Preparative HPLC (MeCN/H$_2$O gradient, 60 mL/min.) of fraction two yielded Compound D (0.17).

Preparation of Enriched Stilbenoid Extracts of Cajanus spp

Ground Leaf material of *Cajanus Cajun* (1245 kg) was stirred in 10 L of ethanol/water (80:20 v:v) for 24 hours at room temperature with constant mixing. The ethanol solution was filtered through a fritted funnel ("coarse" pore size) under vacuum, evaporated in vacuo to dryness and left in a vacuum oven to dry overnight to provide 200 g of a dark brown material (Enriched Extract 1 (EE1)).

185 g of EE1 was sonicated and stirred into 3 L of dichloromethane (DCM) and 3 L water to dissolve. This mixture was transferred to a separatory funnel and left overnight at room temperature. Any clear lower layer was removed and retained for latter pooling. In the presence of an emulsion within the DCM fraction or at the DCM/water interface, the cloudy emulsion portion of the lower layer (DCM) was removed. The cloudy lower layer portion was removed, centrifuged, transferred back to the separatory funnel and allowed to separate again. This process was repeated to complete the separation between the water and DCM layers.

The lower layer (DCM) was evaporated to dryness under vacuum to yield pre-Enriched Extract 2 (pre-EE2). After concentration, the water layer was freeze dried to yield Enriched Extract 3 (EE3).

The resulting pre-EE2 was dissolved in 2 L of 90% ethanol/water and added to 1.5 L petroleum ether (pet ether). This mixture was transferred to a separatory funnel and allowed to separate into an upper layer(Pet ether) and lower layer (90% ethanol). The lower layer was repeatedly subjected to biphasic separation until the pet ether layer was light in color. In one instance, the lower layer was extracted in 800 ml pet ether and then again in 500 ml pet ether. All of the pet ether fractions were combined and evaporated under vacuum to yield an enriched extract compound. The remaining ethanol fraction was evaporated under vacuum to yield and the final Enriched Extract 2 (EE2).

A water-soluble decoction, Enriched Extract 4 (EE4) was prepared as follows:

300 g of unground leaves in a water permeable bag (tea bag) was immersed in boiling water allowed to boil for 15 minutes. At the end of 15 minutes, the heater was turned off and the mixture was allowed to stand overnight at room temperature. The supernatant was passed through cheese cloth and then filter paper. The bag was squeezed to remove residual fluid, which was centrifuged and filtered. The filtrate was concentrated to about 375 ml. The resulting filtrate was precipitated by adding 1.6 L isopropanol to the filtrate and incubating the mixture in a refrigerator (4C) overnight. The mixture was then filtered through a fritted funnel ("coarse") under vacuum. The supernatant was evaporated to dryness, redissolved in water and freeze-dried to yield 24.16 g of Enriched Extract 4 (EE4).

Large Scale Extraction and Purification

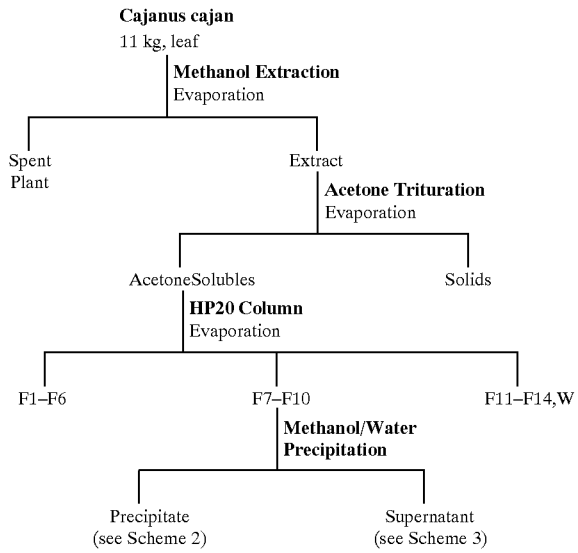

Ground leaf material of *Cajanus cajun* (11 kg) was stirred in 110 L of methanol (MeOH). The MeOH solution was filtered through 1 kg of CELITE™, and evaporated in vacuo to give 1.39 kg of a green oily material. This material was triturated with 20 L of acetone for four hours. The acetone mixture was vacuum filtered through 1 kg of CELITE™ and the filtrate evaporated to dryness giving 721 g of solids. The solids (538 g) were extracted with 4 L MeOH to which 1 L of H$_2$O was slowly added with mixing. The resulting milky suspension was pumped onto an 18×92 cm column containing HP 20 (Mitsubishi) sorbent. The column was eluted with 95:5 MeOH/H$_2$O). Fourteen 10 L fractions were collected. Fractions 7–10 were pooled and evaporated in vacuo giving 64 g of an oily solid. This material was dissolved in 6.5 L of MeOH to which the 3.5 L of H$_2$O was added along with 10 mL of HOAc. After 30 minutes, the mixture was filtered through Whatman #2 filter paper. Both the MeOH precipitation solids and MeOH precipitation filtrate were kept for further processing. The MeOH precipitation solids were dried in a vacuum oven overnight at 40° C. This gave 10 g of a white amorphous powder, which was placed into an Erlenmeyer flask along with 500 mL on n-hexane. With good mixing, acetone was added until the solution became clear. One gram of decolorizing charcoal was added to the stirred solution, which was then vacuum filtered through a bed (2 g) of CELITE™. The filtrate was allowed to stand open in a hood overnight resulting in the precipitation of solids. The supernatent was decanted and 40 mL of hexane and 5 mL of acetone were added back to the solids which formed two layers upon standing at –10° C. This gave 10 g of a white amorphous powder which was placed into an Erlenmeyer flask along with 500 mL of n-hexane. With good mixing, acetone was added until the solution became clear. One gram of decolorizing charcoal was added to the stirred solution which was then vacuum filtered through a bed (2 g) of CELITE™. The filtrate was allowed to stand open in a hood overnight resulting in the precipitation of solids. The supernatant was decanted and 40 mL of hexane and 5 mL of acetone were added back to the solids which formed two layers upon standing at –10° C. for two hours. The layers were separated and the top layer was allowed to stand uncovered overnight, yielding colorless crystalline solids. The crystalline material was triturated with a minimal amount of 10:1 hexane/acetone and allowed to stand in a closed container at room temperature overnight. The supernatant was decanted and the crystals dried in a vacuum oven giving 6 g of material identified as Compound C from NMR and HPLC diode array data. Yield from plant was 0.07%.

Scheme 2

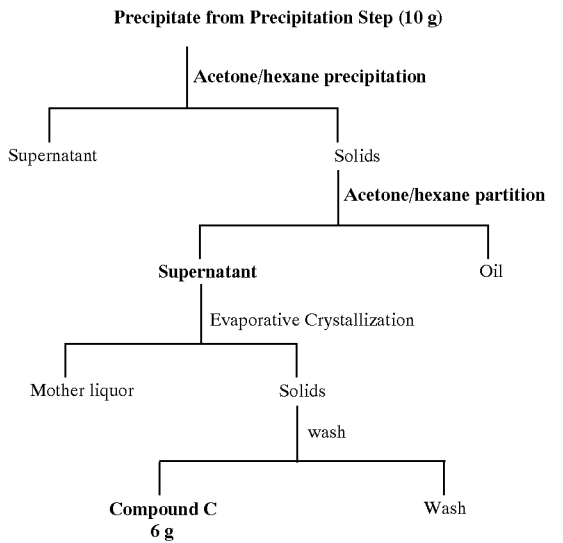

The MeOH precipitation filtrate (10 L) was passed through a small amount of C18 (Bakerbond, 40 mm) pumped onto a 100×5 cm C18 chromatography column which had been washed with MeOH and equilibrated with 65:35:0.1 MeOH/water/HOAc. An additional 500 mL of 65:35:0.1 MeOH/water/HOAc was pumped through the column in order to complete the loading. The column was eluted with 80:20:0.1 MeOH/water/HOAc. Thirty-two fractions, each containing 1 L, were collected. Fractions 12–18 were pooled and evaporated in vacuo to give 18 g of solids. The solids (11.1 g) were dispersed in 700 mL of hexane with stirring. To the dispersion was added enough DCM (200 mL) to produce a clear solution. To this solution was added 1 g of decolorizing charcoal. The suspension was stirred for 1 hour then filtered through a bed of CELITE™ (39 g). The CELITE™ bed was washed with an additional 100 mL of 7:2 hexane/CH2Cl2. The combined solutions (1000 mL) were slowly (3 Hours) evaporated using a stream of nitrogen to a volume of 300 mL. The solids were filtered, dried in a vacuum oven and recrystallized as follows. The dried material (8 g) was dissolved into 10 mL of DCM to which was added 70 mL of hexane with stirring. The solution was allowed to stand uncovered until solids formed. The container was then covered and allowed to stand overnight at –10° C. The resulting first crop of crystals was filtered and set aside. The supernatant was concentrated using a stream of nitrogen and a second crop of crystals was collected. The first and second crops were combined and dried in a vacuum oven overnight to give 5.4 g of Compound A as an off-white solid. Identification was made from NMR and HPLC diode-array data. Yield from plant materials was 0.1%.

Scheme 3

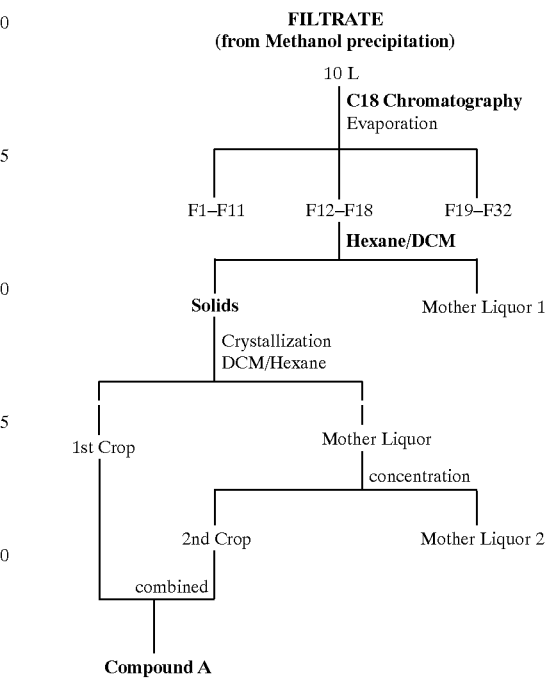

Semi-Synthetic Preparation of Stilbenoid Compounds

All agents were used as received. All moisture sensitive reactions were done under a nitrogen atmosphere, using dry solvents; air sensitive reactions were done under a nitrogen atmosphere. Evaporation of solvents were done at room temperature unless otherwise noted. Column chromatography was performed on C-18 preparative HPLC (Bakerbond). $^1$H NMR and $^{13}$C NMR were obtained at 400 MHz and 100 Mhz, respectively. Elemental analysis were performed by the Analytical Services Department at the University of California, Berkeley. Melting points are uncorrected.

Production of Compound E and Compound F from Compound A

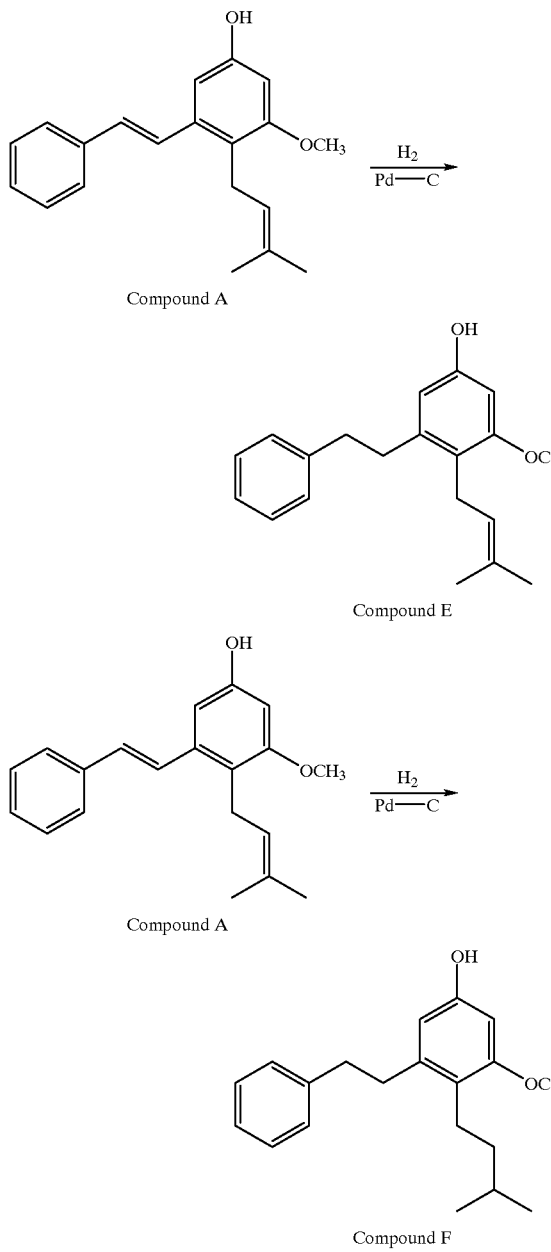

Production of Compound G from Compound B

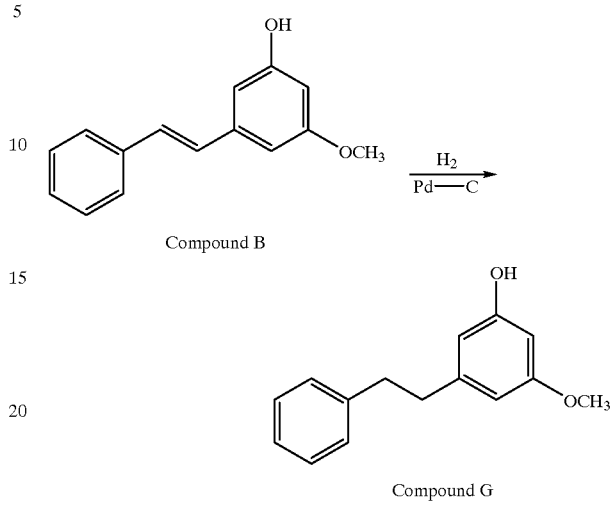

A solution of Compound B (500 mg) in MeOH (15 mL) was hydrogenated over 20% Pd charcoal (99 mg) at room temperature for 3 hours under 50 psi $H_2$. The catalyst was then removed by filtration. The product was purified by C-18 preparative HPLC, using a gradient of acetonitrile and water as the solvent system, to yield 237 mg of Compound G as a brown oil. UV (MeCN/H2O, 8:2) $\lambda_{max}$ 278 nm; IR (thin film) v 3365, 2929, 1598, 1456, 1195, 1146, 1059 cm$^{-1}$; $^1$H NMR and $^{13}$C NMR; EIMS m/z 228, 137, 91; HREIMS m/z 228.1167 (M+, Δ7.4 ppm from calcd)

Production of Compound H from Compound C

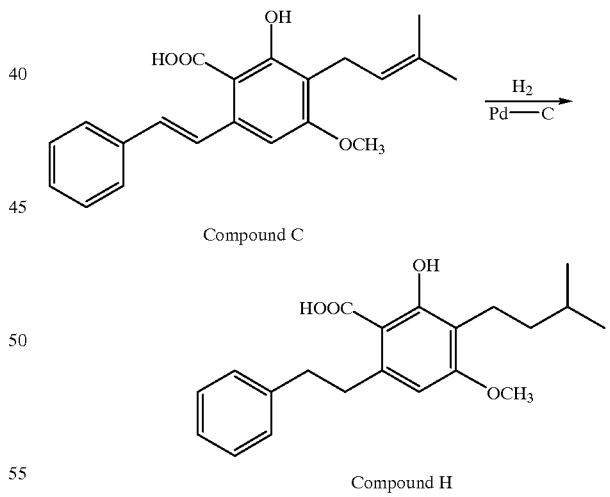

A solution of Compound A (394 mg) in MeOH (10 mL) was hydrogenated over 10% Pd charcoal (41 mg) at room temperature for 3 hours under 50 psi $H_2$. The catalyst was then removed by filtration. The product was purified by C-18 preparative HPLC (Bakerbond), using a gradient of acetonitrile and water as the solvent system, to yield 289 mg of Compound E as an off-white solid. UV (MeCN/H2O, 8:2) $\lambda_{max}$ 284 nm; IR (thin film) v 3354, 2929, 1604, 1456, 1304, 1189, 1140, 1086 cm$^{-1}$; $^1$H NMR and $^{13}$C NMR; EIMS m/z 296, 239, 191, 163, 137; HREIMS m/z 296.1761 (M+, Δ5.2 ppm from calcd) and 26 mg of Compound F; UV (MeCN/H2O, 8:2) $\lambda_{max}$ 282 nm; IR (thin film) v 3354, 2951, 1604, 1467, 1304, 1195, 1146 cm$^{-1}$; $^1$H NMR and $^{13}$C NMR; EIMS m/z 298, 241, 193, 151, 137; HREIMS m/z 298.1927 (M+, Δ2.0 ppm from calcd).

A solution of Compound C (212 mg) in MeOH (10 mL) was hydrogenated over 20% Pd charcoal (43 mg) at room temperature for 3 hours under 50 psi $H_2$. The catalyst was then removed by filtration. The product was purified by C-18 preparative HPLC, using a gradient of acetonitrile and water as the solvent system, to yield 175 mg of Compound H as a white solid. UV (MeCN/H2O, 8:2) $\lambda_{max}$ 269 nm; IR (thin film) v 3398, 2951, 1609, 1456, 1271, 1140 cm$^{-1}$; $^1$H NMR and $^{13}$C NMR; EIMS m/z 298, 268, 241, 207, 151, 137, 91; HREIMS m/z 342.1834 (M+, Δ0.9 ppm from calcd.).

Structure Elucidation of the Stilbene Compounds

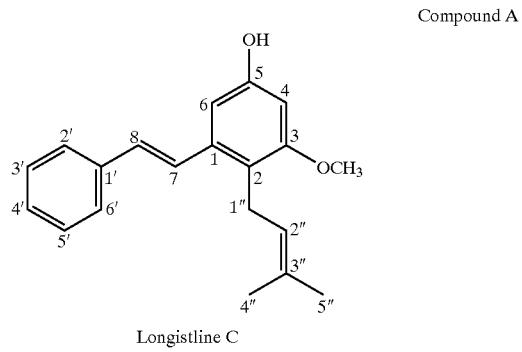

Longistline C

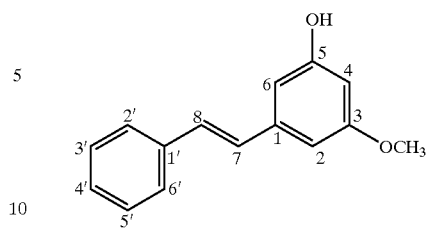

Compound A (Longistyline C) was isolated previously from *Lonchocarpus violaceus* (*Lloydia*, 1977, 40, 201) and *Cajanus cajan* (*Chung Ts'ao Yao*, 1985, 18, 2). The molecular formula of Compound A was established as $C_{20}H_{22}O_2$ based on a peak in the HREIMS at m/z 294.1634 (M$^+$, Δ4.8 ppm from calcd.). An IR spectrum of Compound A revealed absorbances at ν (cm$^{-1}$): 3337, 2926, 1594, 1455, 1430, 1355, and 1316. The structure of Compound A was elucidated by careful interpretation of spectral data. Assignments were based on one and two-dimensional NMR experiments known to those skilled in the art of structure elucidation and included $^1$H NMR $^{13}$C NMR, Heteronuclear Multiple Quantum Correlation (HMQC), and Heteronuclear Multiple Bond Correlation (HMBC). Values for the $^1$H NMR and $^{13}$C NMR chemical shifts of Compound A are given in the table below. Long range proton-carbon correlations observed in the HMBC spectrum are also listed.

NMR Data for Compound A
Spectra obtained in CDCl$_3$
$^{13}$C NMR @ 100 MHz:
δ; $^1$H NMR @ 400 MHz: δ, integral, multiplicity, J

| Position | $^{13}$C NMR | $^1$H NMR | HMBC Correlations |
|---|---|---|---|
| 1 | 137.9 | — | |
| 2 | 121.0 | — | |
| 3 | 158.5 | — | |
| 4 | 98.5 | 6.38 1H, d 2.8 Hz | C-2, C-3, C-5, C-6 |
| 5 | 154.3 | — | |
| 6 | 104.1 | 6.70 1H, d 2.8 Hz | C-2, C-4, C-5, C-7 |
| 7 | 126.4 | 7.33 1H, d 16 Hz | C-1', C-2, C-6 |
| 8 | 130.5 | 6.94 1H, d 16 Hz | C-1, C-2' (C-6') |
| 1' | 137.5 | — | |
| 2'/6' | 126.5 | 7.49 2H, m | C-8, C-4' |
| 3'/5' | 128.6 | 7.37 2H, m | C-1' |
| 4' | 127.6 | 7.27 1H, m | C-2' (C-6') |
| 3-OCH$_3$ | 55.7 | 3.81 3H, s | C-3 |
| 1" | 24.4 | 3.43 2H, d 7 Hz | C-1, C-2, C-3, C-2", C-3" |
| 2" | 123.4 | 5.12 1H, t 7 Hz | C-4", C-5" |
| 3" | 130.9 | — | |
| 4" | 17.9 | 1.81 3H, s | C-2", C-3", C-5" |
| 5" | 25.7 | 1.69 3H, s | C-2", C-3", C-4" |

Compound B (Pinosylvin monomethyl ether) was isolated originally in 1939 from the heartwood of Pine (*Liebigs Ann. Chem.*, 1939, 539, 116). Subsequently, it has been found in over 60 different Pinus species (*Prog. in Phytochemistry*, 1980, 6, 203) and bovine urine (*J. Nat. Prod.*, 1983, 46, 852). However, this compound has not been reported previously from *Cajanus cajan*. The molecular formula for Compound B was determined to be $C_{15}H_{14}O_2$ by the appearance of a peak in the HRFABMS at m/z 294.1633 (M$^+$, Δ4.5 ppm from calcd.). The IR spectrum of Compound B revealed absorbances at ν (cm$^{-1}$): 3435, 1609, 1451, 1422, and 1086. The structure of Compound B was elucidated by careful interpretation of the spectral data. Values for the $^1$H NMR and $^{13}$C NMR chemical shifts of Compound B are given in the table below. Long range proton-carbon correlations observed in the HMBC spectrum are also listed.

NMR Data for Compound B
Spectra obtained in CDCl$_3$
$^{13}$C NMR @ 100 MHz:
δ; $^1$H NMR @ 400 MHz: δ, integral, multiplicity, J

| Position | $^{13}$C NMR | $^1$H NMR | HMBC Correlations |
|---|---|---|---|
| 1 | 139.7 | — | |
| 2 | 105.0 | 6.68 1H, dd 2.0 Hz | C-3, C-4, C-6, C-7 |
| 3 | 161.1 | — | |
| 4 | 101.0 | 6.40 1H, dd 2.0 Hz | C-2, C-3, C-5, C-6 |
| 5 | 156.8 | — | |
| 6 | 106.0 | 6.65 1H, dd 2.0 Hz | C-2, C-4, C-5, C-7 |
| 7 | 128.3 | 7.00 1H, d 16 Hz | C-2, C-6, C-8, C-1' |
| 8 | 129.4 | 7.06 1H, d 16 Hz | C-1, C-7, C-2' (C-6') |
| 1' | 137.0 | — | |
| 2'/6' | 126.6 | 7.50 2H, m | C-8, C-4' |
| 3'/5' | 128.7 | 7.37 2H, m | C-1' |
| 4' | 127.8 | 7.29 1H, m | C-2' (C-6') |
| 3-OCH$_3$ | 55.4 | 3.82 3H, s | C-3 |

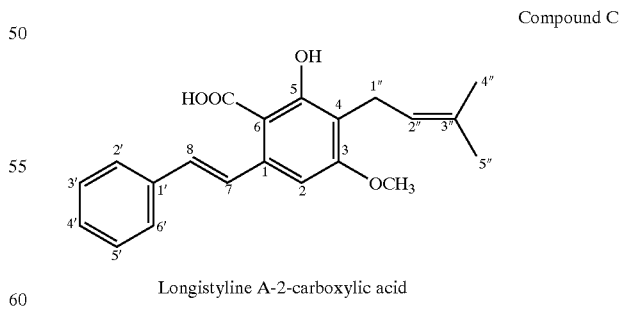

Longistyline A-2-carboxylic acid

Compound C was reported previously from *Cajanus cajan* (*Phytochemistry*, 1982, 21, 2935). Compound C was determined to have a molecular formula of $C_{21}H_{22}O_4$ based on the presence of a peak at m/z 337.1473 (Δ9.9 ppm from calcd.) in the HRFABMS corresponding to [M-H]$^-$. The IR spectrum of Compound C showed absorbances at ν (cm$^{-1}$):

3422, 2968, 1702, 1629, 1451, 1277, 1170, and 1117. The structure of Compound C was elucidated through careful examination of the spectral data. Values for the $^1$H NMR and $^{13}$C NMR chemical shifts of Compound C are given in the table below. Long range proton-carbon correlations observed in the HMBC spectrum are also listed.

NMR Data for Compound C
Spectra obtained in CDCl$_3$
$^{13}$C NMR @ 100 MHz:
δ; $^1$H NMR @ 400 MHz: δ, integral, multiplicity, J

| Position | $^{13}$C NMR | $^1$H NMR | HMBC Correlations |
|---|---|---|---|
| 1 | 141.9 | — | |
| 2 | 103.3 | 6.67 1H, s | C-1", C-1, C-3, C-4, C-6, C-7, 6-COOH |
| 3 | 162.4 | — | |
| 4 | 116.7 | — | |
| 5 | 162.2 | — | |
| 6 | 103.1 | — | |
| 7 | 130.4 | 7.87 1H, d 16 Hz | C-1', C-1, C-2, C-6, C-8 |
| 8 | 130.7 | 6.84 1H, d 16 Hz | C-1, C-7, C-1', C-2' (C-6') |
| 6-COOH | 175.7 | 4.70 1H, br s | |
| 3-OCH$_3$ | 55.7 | 3.96 3H, s | C-3 |
| 5-OH | — | 11.58 1H, s | C-4, C-5, C-6, |
| 1' | 137.3 | — | |
| 2'/6' | 126.8 | 7.55 2H, m | C-8, C-4' |
| 3'/5' | 128.7 | 7.40 2H, m | C-1' |
| 4' | 127.8 | 7.30 1H, m | C-2' (C-6') |
| 1" | 22.1 | 3.39 2H, d 7 Hz | C-3, C-4, C-2", C-3" |
| 2" | 121.9 | 5.23 1H, t 7 Hz | C-1", C-4", C-5" |
| 3" | 132.0 | — | |
| 4" | 17.8 | 1.81 3H, s | C-2", C-3", C-5" |
| 5" | 25.8 | 1.70 3H, s | C-2", C-3", C-4" |

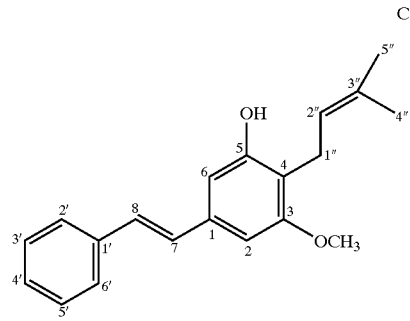

Longistyline A

Compound D (Longistyline A) was isolated previously from *Lonchocarpus violaceus* (*Lloydia*, 1977, 40, 201) and *Cajanus cajan* (*Chung Ts'ao Yao*, 1985, 18, 2). The molecular formula of Compound D was established as C$_{20}$H$_{22}$O$_2$ on the basis of a peak in the HREIMS at m/z 226.0981 (M$^+$, Δ5.6 ppm from calcd.). The IR spectrum showed absorbances at ν (cm$^{-1}$): 3328, 3027, 2940, 2839, 1592, 1497, 1454, and 1347. The structure of Compound D was elucidated through comparison with literature and careful examination of the spectral data including $^1$H NMR, $^{13}$C NMR, Heteronuclear Multiple Quantum Correlation (HMQC), and Heteronuclear Multiple Bond Correlation (HMBC). Values for the $^1$H NMR and $^{13}$C NMR chemical shifts of Compound D are given in the table below. Long range proton-carbon correlations observed in the HMBC spectrum are also listed.

NMR Data for Compound D
Spectra obtained in CDCl$_3$
$^{13}$C NMR @ 100 MHz:
δ; $^1$H NMR @ 400 MHz: δ, integral, multiplicity, J

| Position | $^{13}$C NMR | $^1$H NMR | HMBC Correlations |
|---|---|---|---|
| 1 | 136.6 | — | |
| 2 | 101.6 | 6.65 1H, d 1.6 Hz | C-3, C-4, C-6, C-7 |
| 3 | 158.1 | — | |
| 4 | 115.1 | — | |
| 5 | 155.5 | — | |
| 6 | 107.2 | 6.68 1H, d 1.2 Hz | C-2, C-4, C-5, C-7 |
| 7 | 128.7 | 7.03 1H, d 16 Hz | C-1', C-8 |
| 8 | 128.4 | 7.06 1H, d 16 Hz | C-1, C-2' (C-6') |
| 1' | 137.3 | — | |
| 2'/6' | 126.5 | 7.52 2H, m | C-8, C-4' |
| 3'/5' | 128.6 | 7.37 2H, m | C-1' |
| 4' | 127.5 | 7.27 1H, m | C-2' (C-6') |
| 5-OH | — | 5.38 1H, br s | C-3 |
| 3-OCH$_3$ | 55.8 | 3.88 3H, s | C-3 |
| 1" | 22.4 | 3.43 2H, d 7 Hz | C-3, C-4, C-5, C-2", C-3" |
| 2" | 121.9 | 5.26 1H, t 7 Hz | C-4", C-5" |
| 3" | 134.4 | — | |
| 4" | 17.8 | 1.83 3H, s | C-2", C-3", C-5" |
| 5" | 25.8 | 1.76 3H, s | C-2", C-3", C-4" |

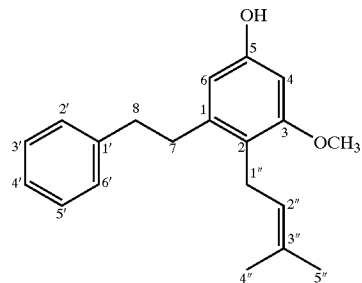

Dihydrolongistyline C

Compound E (Dihydrolongistyline C) was prepared by hydrogenation of Compound A. Compound F was reported previously as a natural product isolated from *Radula kojana* (*Phytochemistry*, 1991, 30, 219). The molecular formula, C$_{20}$H$_{24}$O$_2$, was confirmed by a peak at m/z 296.1761 (M$^+$,Δ5.25 ppm from calcd.) in the HREIMS of SP-36306. The IR spectrum of Compound B showed absorbances at ν (cm$^{-1}$): 3354, 2929, 1604, 1456, 1034, 1190, 1140, and 1086. The structure of Compound E was elucidated through comparison with literature and careful interpretation of the spectral data. Values for the $^1$H NMR and $^{13}$C NMR chemical shifts of Compound E are given in the table below.

NMR Data for Compound E
Spectra obtained in CDCl$_3$
$^{13}$C NMR @ 100 MHz:
δ; $^1$H NMR @ 400 MHz: δ, integral, multiplicity, J

| Position | $^{13}$C NMR | $^1$H NMR |
|---|---|---|
| 1 | $^a$141.97 | — |
| 2 | 120.6 | — |
| 3 | 158.6 | — |
| 4 | 97.0 | 6.32 1H, d 2.4 Hz |
| 5 | 154.2 | — |
| 6 | 107.9 | 6.29 1H, d 2.4 Hz |
| 7 | 35.2 | 2.86 4H, s |
| 8 | 37.5 | 2.86 4H, s |

NMR Data for Compound E
Spectra obtained in CDCl$_3$
$^{13}$C NMR @ 100 MHz:
δ; $^1$H NMR @ 400 MHz: δ, integral, multiplicity, J

| Position | $^{13}$C NMR | $^1$H NMR |
|---|---|---|
| 1' | [a]142.02 | — |
| 2'/6' | 128.3 | 7.20–7.35 5H, m |
| 3'/5' | 128.3 | 7.20–7.35 5H, m |
| 4' | 125.9 | 7.20–7.35 5H, m |
| 3-OCH$_3$ | 55.6 | 3.80 3H, s |
| 1" | 24.4 | 3.32 2H, d 6.4 Hz |
| 2" | 123.8 | 5.08 1H, t 7 Hz |
| 3" | 130.7 | — |
| 4" | 17.9 | 1.76 3H, d 0.8 Hz |
| 5" | 25.7 | 1.69 3H, d 1.2 Hz |

[a]values interchangeable

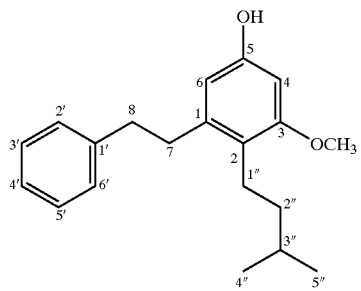

Tetrahydrolongistyline C

Compound F (Tetrahydrolongistyline C) was prepared by hydrogenation of Compound A and possesses a molecular formula of C$_{20}$H$_{26}$O$_2$ as evidenced by a peak in the HREIMS of Compound F at m/z 298.1927 (M$^+$, Δ2.05 ppm from calcd.). The IR spectrum of Compound F showed absorbances at ν (cm$^{-1}$): 3354, 2951, 1604, 1467, 1304, 1195, and 1146. The structure of Compound F was elucidated through careful interpretation of the spectral data, including $^1$H NMR and $^{13}$C NMR. Values for the 1H NMR and $^{13}$C NMR chemical shifts of Compound F are given in the table below.

NMR Data for Compound F
Spectra obtained in CDCl$_3$
$^{13}$C NMR @ 100 MHz:
δ; $^1$H NMR @ 400 MHz: δ, integral, multiplicity, J

| Position | $^{13}$C NMR | $^1$H NMR |
|---|---|---|
| 1 | [a]141.5 | — |
| 2 | 122.1 | — |
| 3 | 158.7 | — |
| 4 | 96.9 | 6.28 1H, d 2.4 Hz |
| 5 | 154.0 | — |
| 6 | 107.8 | 6.31 1H, d 2.4 Hz |
| 7 | 35.2 | 2.85 4H, s |
| 8 | 37.9 | 2.85 4H, s |
| 1' | [a]142.0 | — |
| 2'/6' | [b]128.3 | 7.20–7.35 5H, m |
| 3'/5' | [b]128.4 | 7.20–7.35 5H, m |
| 4' | 126.0 | 7.20–7.35 5H, m |
| 3-OCH$_3$ | 55.5 | 3.79 3H, s |
| 1" | 28.6 | 2.57 2H |
| 2" | 39.6 | 1.33 2H |
| 3" | 23.4 | 1.64 1H |
| 4" | 22.6 | 0.98 3H |
| 5" | 22.6 | 0.96 3H |

[a-b]values interchangeable

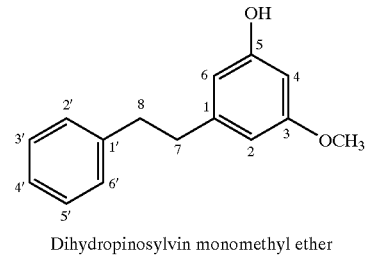

Dihydropinosylvin monomethyl ether

Compound G (Dihydropinosylvin monomethyl ether) has been reported previously as a natural product isolated from *Pinus strobus* var. chiapensis (*J. Braz. Chem. Soc.* 1996, 7, 187). Compound G was prepared by hydrogenation of Compound B. The molecular formula for Compound G, C$_{15}$H$_{16}$O$_2$, was established based on a peak at m/z 228.1167 (M$^+$, Δ7.36 ppm from calcd.) in the HREIMS of SP-36308. The IR spectrum of Compound G showed absorbances at ν (cm$^{-1}$): 3365, 2929, 1598, 1456, 1195, 1146, and 1059. The structure of Compound G was elucidated through comparison with the literature and careful interpretation of the spectral data, including $^1$H NMR and 13C NMR. Values for the $^1$H NMR and $^{13}$C NMR chemical shifts of SP-36308 are given in the table below.

NMR Data for Compound G
Spectra obtained in CDCl$_3$
$^{13}$C NMR @ 100 MHz:
δ; $^1$H NMR @ 400 MHz: δ, integral, multiplicity, J

| Position | $^{13}$C NMR | $^1$H NMR |
|---|---|---|
| 1 | 144.5 | — |
| 2 | 106.8 | 6.28 2H, m |
| 3 | 160.8 | — |
| 4 | 99.1 | 6.34 1H, m |
| 5 | 156.5 | — |
| 6 | 107.9 | 6.28 2H, m |
| 7 | 37.5 | 2.87 4H, m |
| 8 | 37.9 | 2.87 4H, m |
| 1' | 141.6 | — |
| 2'/6' | [a]128.3 | 7.19–7.32 5H, m |
| 3'/5' | [a]128.4 | 7.19–7.32 5H, m |
| 4' | 125.9 | 7.19–7.32 5H, m |
| 3-OCH$_3$ | 55.2 | 3.76 3H, s |

[a]values interchangeable

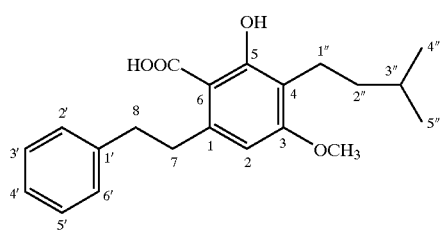

Tetrahydrolongistyline A-2-Carboxylic Acid

Compound H was prepared by hydrogenation of Compound C. The molecular of Compound H was determined to be $C_{21}H_{26}O_4$ based on a peak in the HREIMS at m/z 342.1834 ($M^+$, $\Delta 0.89$ ppm from calcd.). The IR spectrum of Compound H showed absorbances at v ($cm^{-1}$): 3398, 2951, 1609, 1457, 1271, and 1140. The structure of Compound H was elucidated through careful examination of the spectral data. Values for the $^1H$ NMR and $^{13}C$ NMR chemical shifts of Compound H, along with the long range proton-carbon correlations, are given in the table below.

NMR Data for Compound H
Spectra obtained in $CDCl_3$
$^{13}C$ NMR @ 100 MHz:
δ; $^1H$ NMR @ 400 MHz: δ, integral, multiplicity, J

| Position | $^{13}C$ NMR | $^1H$ NMR | HMBC Correlations |
|---|---|---|---|
| 1 | 145.3 | — | |
| 2 | 103.5 | 6.21 1H, s | C-3, C-4, C-6, C-7, 6-COOH |
| 3 | 163.0 | — | |
| 4 | 116.8 | — | |
| 5 | 162.3 | — | |
| 6 | 106.1 | — | |
| 7 | 39.2 | 3.27 2H, m | C-1', C-1, C-2, C-6, C-8 |
| 8 | 38.2 | 2.94 2H, m | C-1, C-7, C-1', C-2' (C-6') |
| 6-COOH | 175.4 | — | |
| 3-OCH$_3$ | 55.5 | 3.79 3H, s | C-3 |
| 5-OH | — | 11.62 1H, s | C-4, C-5, C-6, |
| 1' | 141.9 | — | |
| 2'/6' | 128.5 | 7.21 2H, m | C-4', C-8 |
| 3'/5' | 128.3 | 7.31 2H, m | C-1', C-2' (C-6') |
| 4' | 125.9 | 7.22 1H, m | |
| 1" | 20.7 | 2.57 2H, m | C-3, C-4, C-5, C-2", C-3" |
| 2" | 37.9 | 1.38 2H, m | C-4, C-1", C-3", C-4", C-5" |
| 3" | 28.3 | 1.60 1H, m | C-1", C-4", C-5" |
| 4" | 22.6 | 0.97 3H, s | C-2", C-3", C-5" |
| 5" | 22.6 | 0.95 3H, s | C-2", C-3", C-4" |

Hypoglycemic Activity of the Stilbenoids

The following examples illustrate the effectiveness of the stilbenoids of formulae described herein in reducing plasma glucose levels in C57BL/ks diabetic (db/db) mice, i.e., an art-recognized model of non-insulin dependent diabetes mellitus (NIDDM).

A representative sampling of stilbene analogues were tested in the in vivo mouse model described below.

In vivo Experiments; General Protocols

The following experiments are set forth to assist in understanding the invention and should not, of course, be construed as specifically limiting the invention described and claimed herein. Such variations of the inventions which would be within the purview of those in the art, including the substitution of all equivalents now known or later developed, including changes in formulation or minor changes in experimental design, are to be considered to fall within the scope of the invention as hereinafter claimed.

This example illustrates the effectiveness of the stilbenoids of formulae described herein, e.g. longistyline A (Compound A); pinosylvin monomethyl ether (Compound B), longistyline A-2-carboxylic acid (Compound C); longistyline A(Compound D); 7,8-dihydrolongistyline C(Compound E); 7,8,2",3"-tetrahydrolongistyline C(Compound F); 7,8-dihydropinosylvin monomethyl ether (Compound G); and 7,8,2",3"-tetrahydrolongistyline A-2-carboxylic acid (Compound H), in reducing plasma glusocose levels in C57BL/ks diabetic (db/db) mice, i.e., an art recognized model of non-insulin dependent diabetes mellitus (NIDDM).

Materials and Methods

Genetically altered obese diabetic mice (designated C57BL/ks diabetic or db/db) were purchased from the Jackson Laboratory (Bar Harbor, Me., USA), and served as experimental animals. Male animals between the ages of 8–9 weeks were employed in the studies described here. Animals were housed (4 mice/cage) under standard laboratory conditions at 22° C. and 50% relative humidity, and were maintained on a diet of Purina rodent chow and water ad libitum. Prior to treatment, blood was collected from the tail vein of each animal. Mice that had plasma glucose levels between 350 and 600 mg/dL were used. Each treatment group consisted of eight mice that were distributed so that the mean glucose levels were equivalent in each group at the start of the study. Db/db mice received, orally by gavage: the experimental compound administered at 62.5, 125, or 250 mg/kg/day (unless otherwise noted), or metformin administered at 250 mg mmol/kg for 1–3 days. Test compounds were delivered in a liquid vehicle containing 0.25% (w/v) carboxymethyl-cellulose, 1% (v/v) Tween 600 (polyoxyethylene sorbitan monosterate), and up to 10% (v/v) dimethyl sulfoxide (DMSO) in a volume of 10 ml/kg. Blood was sampled from the tail vein at three hours, six, eight, twenty-four, and thirty hours post-administration (the first administration) of the particular compound in non-fasted conditions. Experiments 3–5 also sampled blood at fifty-four hours post-administration (the first administration) of the particular compound in non-fasted conditions. Blood samples were analyzed for plasma glucose levels. Individual body weights and mean food consumption (each cage) were also measured daily.

The isolated test substances were prepared as described previously (vide supra). Metformin (1,1-dimethylbiguanide), carboxymethyl cellulose and Tween 60 were purchased from Sigma Chemical Co. (St. Louis, Mo., USA; catalog #'s D-5035, C-4888, and p-1629, respectively). Plasma glucose levels were determined colorimetrically using glucose oxidase (Sigma Chemical Co.; Sigma catalog #315). Significant differences between groups (comparing compound-treated to vehicle-treated) were evaluated using analysis of variance and Fisher's post-hoc test.

Results

Enriched Extracts

As shown in FIG. 1 and in Table 1a, oral administration of Enriched Extract 2 at a dose of 1000 mg/kg produced statistically significant reductions in plasma glucose levels in db/db mice. Interestingly, EE1 (an ethanolic extract) produced hypoglycemic effects that were significant after 5 days. This extract was most similar that those described in the art but significantly less efficacious than the solvent extracted EE2 (Dhar, M. L., et al., Indian J. Exp. Biol., 6, 232 (1968)).

Vehicle, metformin (250 mg/kg) or enriched extract (1000 mg/kg) were given to db/db mice at 0(initial), 8, 24, 32, 48, 56, 72, 80, and 96 hours post initial dose.

Plasma glucose levels were measured at baseline, 3 (day 1), 51 hours (Day 3), and 99 hours (Day 5).

TABLE 1a

| Treatment | Day 1 glucose mg/dL | P value | Day 3 glucose mg/dL | P value | Day 5 glucose mg/dL | P value |
|---|---|---|---|---|---|---|
| Vehicle | −80.9 | | −77.1 | | +102.1 | |
| Metformin | −180.5 | 0.0022 | −207.5 | 0.0018 | −86.4 | 0.0002 |
| EE1 | −97.2 | Ns | −97.4 | Ns | −40.7 | 0.0020 |
| EE2 | −82.8 | Ns | −274.2 | <0.0001 | −144.3 | <0.0001 |
| EE3 | −55.6 | Ns | −104.1 | Ns | +134.2 | NS |
| EE4 | −31.2 | Ns | −54.0 | Ns | +230.9 | Ns |

Ns = not significant

Compounds A, B and C

Figure 2:
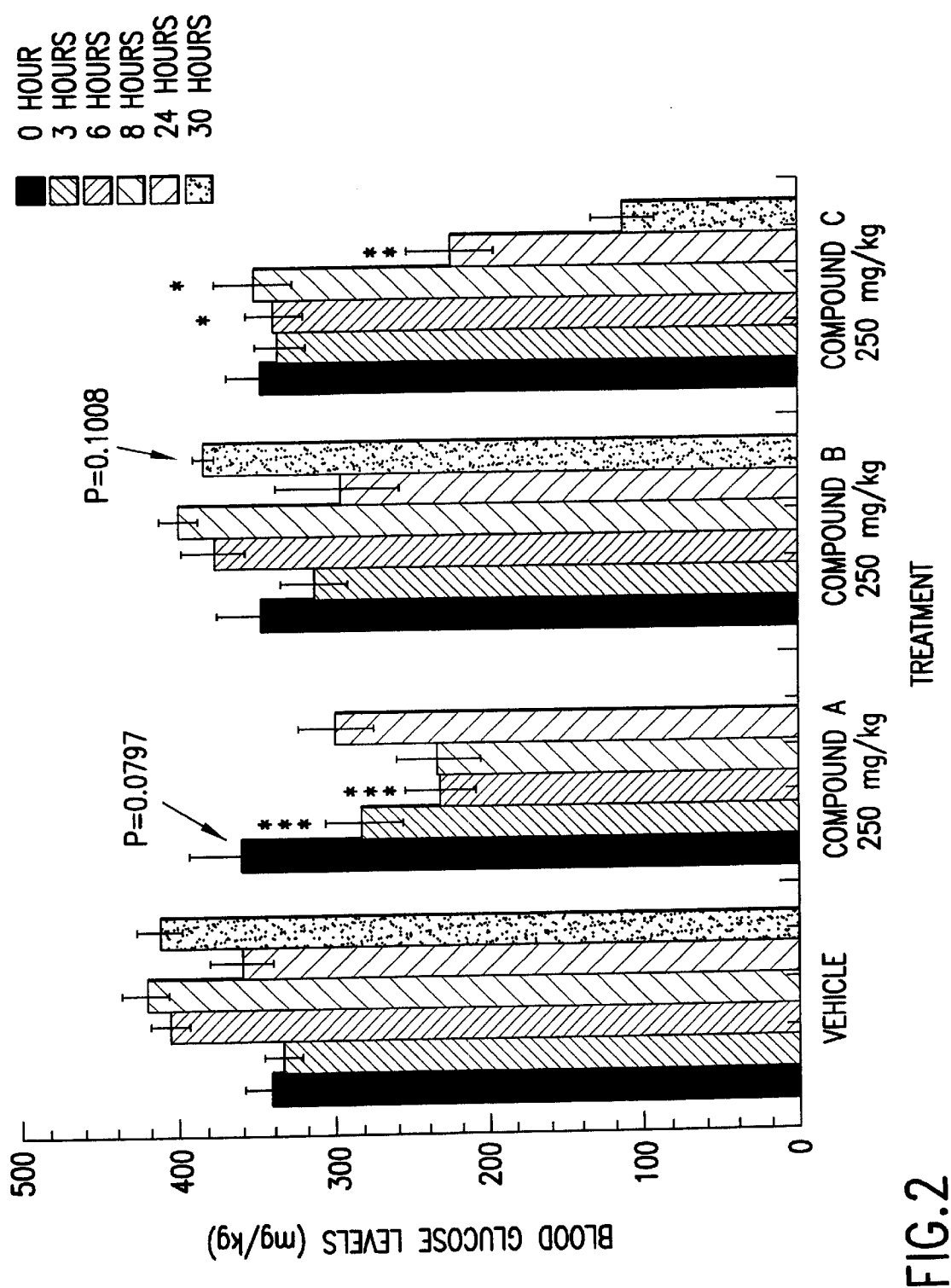
FIG. 2 is a bar graph showing the plasma glucose levels (mg/dL) of db/db mice treated with vehicle only or 250 mg/kg q.d. of Compound A, Compound B, or Compound C. The relevant compound was administered to the animals at 0, 8 and 24 h, and plasma glucose levels were measured at 0, 3, 6, 8, 24, and 30 hours. All data points N=8. *P<0.05; P<0.01; *P<0.0001 (analysis of variance (ANOVA); one factor).

As shown in FIG. 2 and in Tables 1 and 2, below, oral administration of Compounds A and C at a dose level of 250 mg/kg to db/db mice produced statistically significant reduction in plasma glucose, relative to vehicle (control). The following test substances were evaluated in db/db mice for the ability to lower blood glucose: Longistyline C (5-hydroxy-3-methoxystilbene-2-carboxylic acid) (Compound A); pinosylvin monomethyl ether (5-hydroxy-3-methoxystilbene) (Compound B); and Longistyline A-2-carboxylic acid (3-hydroxy-5-methoxy-4-(3-methyl-2-butenyl)stilbene-2-carboxylic acid) (Compound C). The test substances were evaluated in a series of experiments which are summarized in Tables 1 and 2 below.

A single initial dose of Compound A and additional subsequent doses of Compound C (250 mg/kg) given to db/db mice at eight and twenty-four hours after the initial oral administration resulted in statistically significant reductions in plasma glucose relative to vehicle controls at either six, eight, twenty-four or thirty hour timepoints after initial oral administration. Six hours after the initial dosing, mean glucose levels for the active experimental Compound A and C declined 130.6 mg/dL (p<0.0001) and 8.4 mg/dL (p=0.0295), respectively, from the baseline value. Eight hours after the initial dosing, mean glucose levels for the active experimental Compounds A [02] and C [04] declined 129.1 mg/dL (p<0.0001) and rose 4.5 mg/dL (p=0.0466), respectively, from the baseline values. Twenty-four hours after the initial dosing, just after the third dosing, mean glucose levels for the active experimental Compound C declined 122.8 mg/dL (p=0.0049) from the baseline values.

Single doses of Compound A (250 mg/kg) in vehicle also showed a trend in reducing plasma glucose relative to vehicle controls at 3 hours after initial oral administration. Three hours after dosing, mean glucose levels for the active experimental Compound C suspended in vehicle declined 80.3 mg/dL (p=0.0797) from the baseline value.

Doses of Compound B (250 mg/kg) in Formulation IV also showed a trend in reducing plasma glucose relative to vehicle controls at thirty hours after initial oral administration. Thirty hours after dosing, mean glucose levels for the active experimental Compound C suspended in Formula (IV) rose only 36.5 mg/dL p=0.1088) from the baseline value.

As shown in Table 3, below, the antihyperglycemic effect of Compounds A and C at dosage regimes of 250 mg/kg occurred in the absence of any significantly adverse effect on food intake or body weight. Body weights were not affected in animals treated during the test period (Table 2). It was noted that the food intake of those animals administered compounds A (250 mg/kg) and C (250 mg/kg) was less than that of the normal food intake range (5–6 g/day/mouse).

The data in Tables 1, 2 and 3 indicate that the aforementioned stilbenoids are effective hypoglycemic agents in a rodent model of insulin resistance, obesity, and NIDDM.

TABLE 1

Effects of test substances on glucose-lowering in diabetic db/db mice.

| Treatment | Change in Glucose (mg/dL) 3 h | P Value* | Change in Glucose (mg/dL) 6 h | P Value* |
|---|---|---|---|---|
| Vehicle | −8.0 | | 64.5 | |
| Compound A 250 mg/kg | −80.3 | 0.0797 | −130.6 | <0.0001 |
| Compound B | −35.3 | NS | +29.3 | NS |
| Compound C | −10.4 | NS | −8.4 | 0.0295 |

*Statistical significance evaluated using unpaired t-test and Fisher's post-hoc test.
NS - not significant at p = 0.05 level

TABLE 2

Effects of test substances on glucose-lowering in diabetic db/db mice.

| Treatment | Change in Glucose (mg/dL) 8 h | P Value* | Change in Glucose (mg/dL) 24 h | P Value* | Change in Glucose (mg/dL) 30 h | P Value* |
|---|---|---|---|---|---|---|
| Vehicle | 79.5 | | 18.6 | | | |
| Compound A | −129.1 | <0.0001 | −61.9 | NS | | |
| Compound B | +52.2 | NS | −50.6 | NS | +36.5 | 0.1008 |
| Compound C | +4.5 | 0.0466 | −122.8 | 0.0049 | | |

*Statistical significance evaluated using unpaired t-test and Fisher's post-hoc test.
NS - not significant at p = 0.05 level

TABLE 3

Effects of test substances on body weights and food consumption in diabetic db/db mice.

| Dosage | TREATMENT | Body weight (g/mouse) (mean) 0 h | Body weight (g/mouse) (mean) 24 hr | Food Intake (g/mouse) 0–24 h |
|---|---|---|---|---|
| | VEHICLE | 38.0 ± 0.8 | 37.8 ± 0.8 | 6.8 |
| 250 mg/kg | Compound A | 38.8 ± 0.7 | 38.3 ± 0.7 | 4.2 |
| 250 mg/kg | Compound B | 37.8 ± 0.4 | 37.8 ± 0.4 | 5.9 |
| 250 mg/kg | Compound C | 38.7 ± 0.8 | 38.0 ± 0.7 | 3.3 |

Compound A

Figure 3:
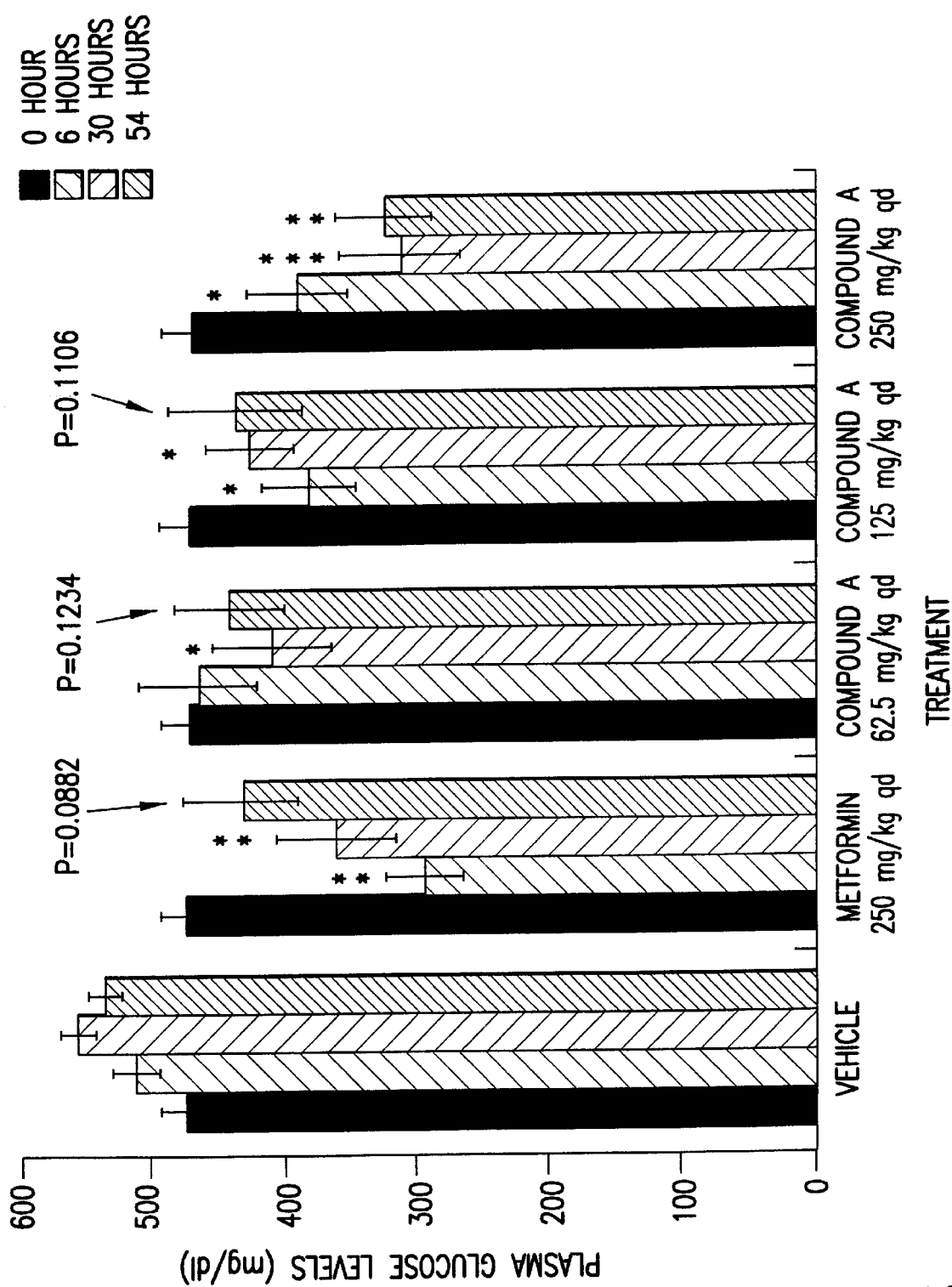
FIG. 3 is a bar graph showing the plasma glucose levels (mg/dL) of db/db mice treated with vehicle only; 250 mg/kg q.d. of metformin; and 62.5, 125 and 250 mg/kg q.d. of longistyline C (Compound A). The relevant compound was administered to the animals at 0, 24 and 48 h, and plasma glucose levels were measured at 0, 6, 30 and 54 h. All data points N=8. *P<0.05; P<0.01; *P<0.0001 (analysis of variance (ANOVA); one factor).

As shown in FIG. 3 and in Table 4, below, oral administration of Compound A at dose levels of 62.5, 125, and 250 mg/kg to db/db mice produced statistically significant reduction in plasma glucose, relative to vehicle (control).

Longistyline C (Compound A) was evaluated in db/db mice for the ability to lower blood glucose. The test substance was evaluated in a series of experiments, which are summarized in Table 4 below.

Single doses of Compound A (62.5, 125 and 250 mg/kg) were given to db/db mice at twenty-four and forty-eight hours after the initial oral administration resulted in statistically significant reductions in plasma glucose relative to vehicle controls at six, thirty or fifty-four h or at all timepoints after oral administration. Six hours after the initial dosing, mean glucose levels of the animals dosed with 125 mg/kg and 250 mg/kg of the active experimental Compound A declined 89.9 mg/dL (p=0.0233) and 79.3 mg/dL (p=0.0367), respectively, from the baseline value. Thirty hours after the initial dosing, six hours after the second dosing, mean glucose levels of animals dosed with 62.5, 125 and 250 mg/kg of the active experimental Compound A declined 62.8 mg/dL (p=0.0153), 44.9 mg/dL (p=0.0460) and 158.5 mg/dL p=0.0001), respectively, from the baseline values. Fifty-four hours after the initial dosing, six hours after the third dosing, mean glucose levels of animals dosed with 250 mg/kg of the active experimental Compound A declined 144.5 mg/dL (p=0.0001) from the baseline values.

62.5 and 125 mg/kg doses of Compound A suspended in vehicle also showed a trend in reducing plasma glucose relative to vehicle controls at fifty-four hours after initial oral administration. Fifty-four hours after initial dosing, mean glucose levels of the animals dosed with 62.5 and 125 mg/kg doses of the active experimental Compound A suspended in vehicle declined 31.0 mg/dL (p=0.1234) and 34.3 mg/dL (p=0.1106), respectively, from the baseline value.

By comparison, the known hypoglycemic agent metformin, given at 250 mg/kg, lowered plasma glucose levels by approximately 180.4 mg/dL (p=0.0003), six hours after the initial dose; and 112.4 mg/dL (p=0.0016), thirty hours after the initial dose, six hours after the second dose. Metformin suspended in vehicle also showed a trend in reducing plasma glucose relative to vehicle controls at fifty-four hours after initial oral administration. Fifty-four hours after initial dosing, six hours after the dosing at forty-eight hours, mean glucose levels of the animals dosed with the metformin suspended in vehicle declined 41.3 mg/dL (p=0.0882) from the baseline value.

As shown in Table 5, below, the antihyperglycemic effect of Compound A at dosage regimes of 62.5 mg/kg, 125 mg/kg, and 250 mg/kg occurred in the absence of any significantly adverse effect on food intake or body weight. Body weights were not affected in animals treated during the test period (Table 6). It was noted that the food intake of those animals administered 250 mg/kg Compound A was less than that of the normal food intake range (5–6 g/day/mouse).

These data indicate that the aforementioned stilbenoids are effective hypoglycemic agents in a rodent model of insulin resistance, obesity, and NIDDM.

TABLE 4

Effects of test substances on glucose-lowering in diabetic db/db mice.

|  | Change in Glucose (mg/dL) | | Change in Glucose (mg/dL) | | Change in Glucose (mg/dL) | |
| --- | --- | --- | --- | --- | --- | --- |
|  | 6 H | P VALUE | 30 H | P VALUE | 54 H | P VALUE |
| Vehicle | 35.9 |  | 79.6 |  | 60.3 |  |
| Metformin | −180.4 | 0.0003 | −112.4 | 0.0016 | −41.3 | 0.0882 |
| Compound A | −8.0 | NS | −62.8 | 0.0153 | −31.0 | 0.1234 |
| Compound A | −89.9 | 0.0233 | −44.9 | 0.0460 | −34.3 | 0.1106 |
| Compound A | −79.3 | 0.0367 | −158.5 | 0.0001 | −144.5 | 0.0012 |

*Statistical significance evaluated using unpaired t-test and Fisher's post-hoc test.
NS - not significant at p = 0.05 level

TABLE 5

Effects of test substances on body weights and food consumption in diabetic db/db mice.

| Dosage | TREATMENT | Body weight (g/mouse) (mean) 0 h | Body weight (g/mouse) (mean) 48 hr | Food Intake (g/mouse) 0–48 h |
| --- | --- | --- | --- | --- |
|  | Vehicle | 39.2 ± 0.5 | 39.5 ± 0.5 | 6.3 |
| 250 mg/kg | Metformin | 37.3 ± 0.7 | 37.2 ± 0.6 | 5.1 |
| 62.5 mg/kg | Compound A | 38.6 ± 0.6 | 39.1 ± 0.5 | 6.1 |
| 125 mg/kg | Compound A | 39.0 ± 0.8 | 38.8 ± 1.0 | 5.1 |
| 250 mg/kg | Compound A | 38.2 ± 0.7 | 38.1 ± 0.7 | 4.1 |

Compound C

Figure 4:
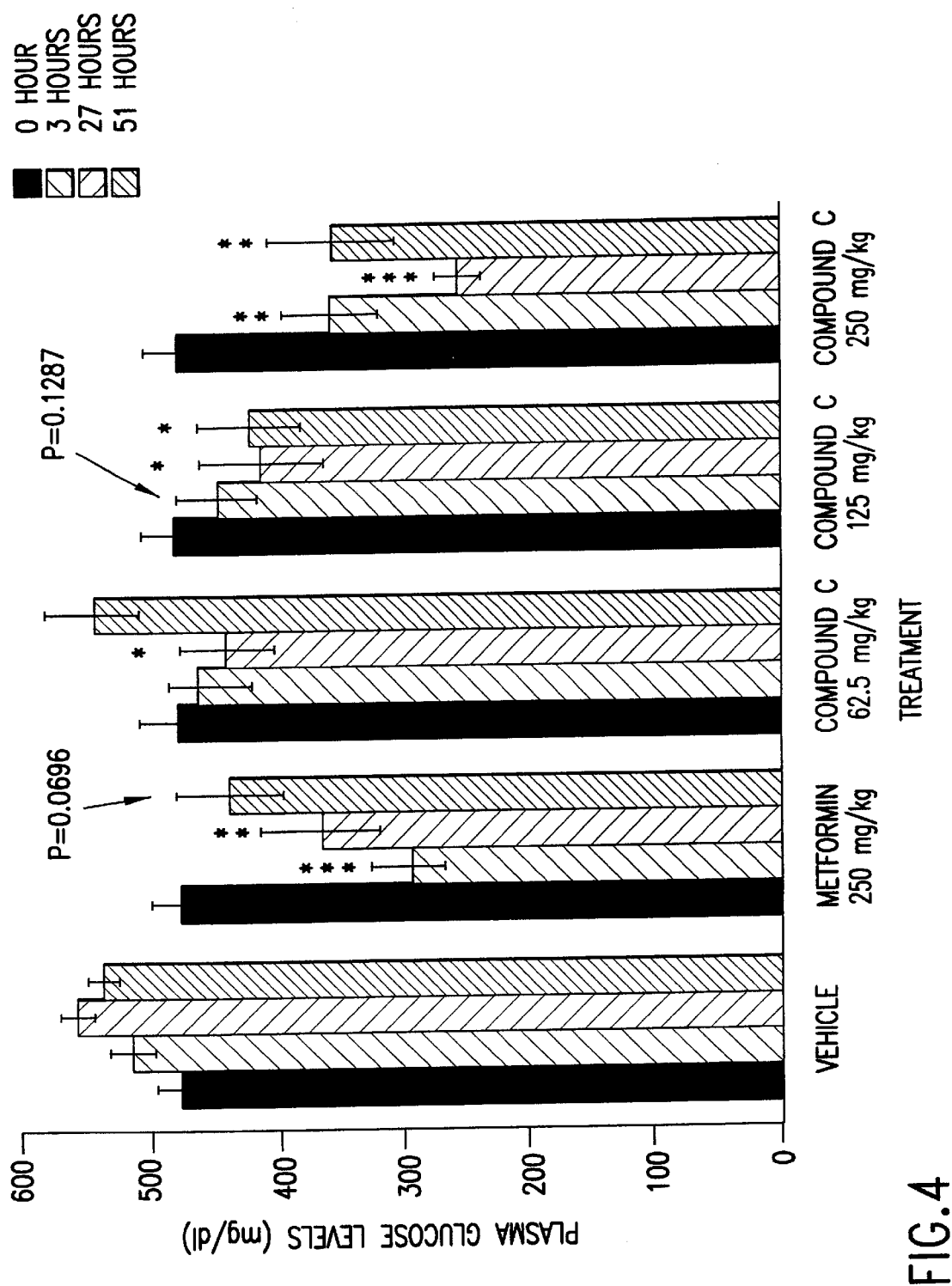
FIG. 4 is a bar graph showing the plasma glucose levels (mg/dL) of db/db mice treated with vehicle only; 250 mg/kg q.d. of metformin; and 62.5, 125 and 250 mg/kg q.d. of longistyline A-2-carboxylic acid (Compound C). The relevant compound was administered to the animals at 0, 24 and 48 h, and plasma glucose levels were measured at 0, 6, 30 and 54 h. All data points N=8. *P<0.05; P<0.01; *P<0.0001 (analysis of variance (ANOVA); one factor).

As shown in FIG. 4 and in Table 6, below, oral administration of Compound C at dose levels of 62.5, 125, and 250 mg/kg to db/db mice produced statistically significant reduction in plasma glucose, relative to vehicle (control).

Longistyline A-2-carboxylic acid(Compound C) was evaluated in db/db mice for the ability to lower blood glucose. The test substance was evaluated in a series of experiments, which are summarized in Table 6 below.

Single doses of Compound C (62.5, 125 and 250 mg/kg) were given to db/db mice at twenty-four and forty-eight hours after the initial oral administration resulted in statistically significant reductions in plasma glucose relative to vehicle controls at six, thirty or fifty-four hours or at all timepoints after oral administration. Six hours after the initial dosing, mean glucose levels of the animals dosed with 250 mg/kg of the active experimental Compound A declined 120.8 mg/dL (p=0.0019) from the baseline value. Thirty hours after the initial dosing, six hours after the second dosing, mean glucose levels of animals dosed with 62.5, 125 and 250 mg/kg of the active experimental Compounds 02 declined 40.7 mg/dL (p=0.0322), 69.7 mg/dL (p=0.0131) and 221.4 mg/dL (p<0.0001), respectively, from the baseline values. Fifty-four hours after the initial dosing, six hours after the third dosing, mean glucose levels of animals dosed with 125 mg/kg and 250 mg/kg of the active experimental Compound 04 declined 60.4 mg/dL (p=0.0409) and 122.0 mg/dL (p=0.0086) from the baseline values.

125 mg/kg doses of Compound C suspended in vehicle also showed a trend in reducing plasma glucose relative to vehicle controls at six hours after initial oral administration. Six hours after initial dosing, mean glucose levels of the animals dosed with the active experimental Compound C suspended in vehicle declined 34.3 mg/dL (p=0.1287) from the baseline value.

By comparison, the known hypoglycemic agent metformin, given at 250 mg/kg, lowered plasma glucose levels by approximately 180.4 mg/dL (p<0.0001), six hours after the initial dose; and 112.4 mg/dL (p=0.0009), thirty hours after the initial dose, six hours after the second dose.

Metformin suspended in vehicle also showed a trend in reducing plasma glucose relative to vehicle controls at fifty-four hours after initial oral administration. Fifty-four hours after initial dosing, mean glucose levels of the animals dosed with metformin suspended in vehicle declined 41.3 mg/dL (p=0.0696) from the baseline value.

As shown in Table 7, below, the antihyperglycemic effect of Compound C at dosage regimes of 62.5 mg/kg, 125 mg/kg, and 250 mg/kg occurred in the absence of any significantly adverse effect on food intake or body weight. Body weights were not affected in animals treated during the test period (Table 7). It was noted that the food intake of those animals administered 250 mg/kg Compound C was less than that of the normal food intake range (5–6 g/day/mouse).

The data in Tables 6 and 7 indicate that the aforementioned stilbenoids are effective hypoglycemic agents in a rodent model of insulin resistance, obesity, and NIDDM.

Compounds E, G and H

Figure 5:
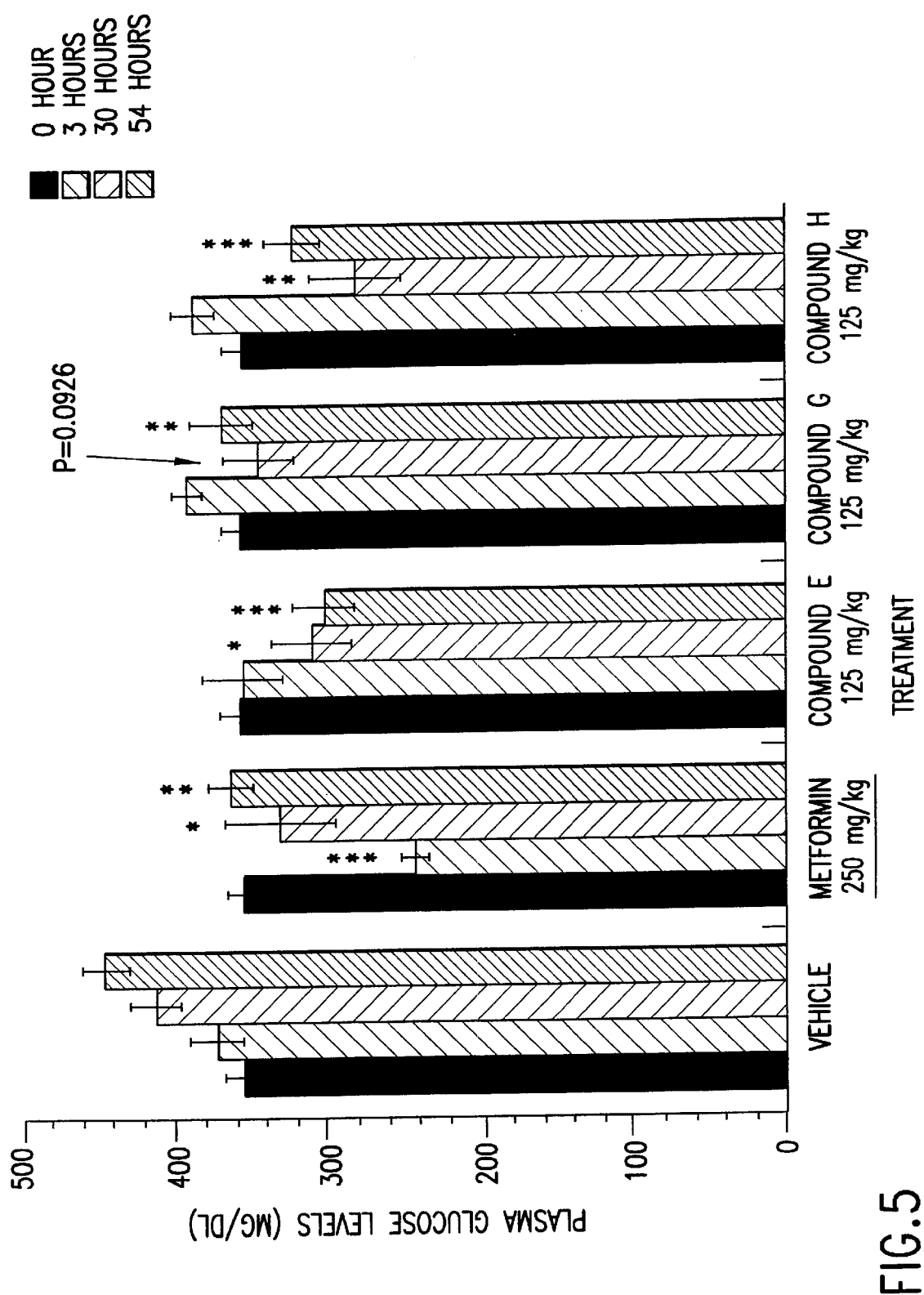
FIG. 5 is a bar graph showing the plasma glucose levels (mg/dL) of db/db mice treated with vehicle only; 250 mg/kg q.d. of metformin; and 125 mg/kg q.d. of 7,8-dihydrolongistyline C (Compound E), 125 mg/kg q.d. of 7,8-dihydropinosylvin monomethyl ether (Compound G), and 125 mg/kg q.d. of 7,8-dihydrolongistyline A-2-carboxylic acid (Compound H). The relevant compound was administered to the animals at 0, 24 and 48 h, and plasma glucose levels were measured at 0, 6, 30 and 54 h. All data points N=8. *P<0.05; P<0.01; *P<0.0001 (analysis of variance (ANOVA); one factor).

As shown in FIG. 5 and in Table 8, below, oral administration of Compounds E (7,8-dihydrolongistyline C), G (7,8-dihydropinosylvin monomethyl ether), and H (7,8-dihydrolongistyline A-2-carboxylic acid), at dose levels of 125 mg/kg to db/db mice produced statistically significant reduction in plasma glucose, relative to vehicle (control).

Longistyline C (Compound A) was evaluated in db/db mice for the ability to lower blood glucose. The test substance was evaluated in a series of experiments, which are summarized in Table 8 below.

Single doses of Compounds E (7,8-dihydrolongistyline C), G (7,8-dihydropinosylvin monomethyl ether), and H (7,8-dihydrolongistyline A-2-carboxylic acid) were given to db/db mice at twenty-four and forty-eight hours after the initial oral administration resulted in statistically significant reductions in plasma glucose relative to vehicle controls at thirty or fifty-four hours or at both timepoints after oral administration. Thirty hours after the initial dosing, mean glucose levels of the animals dosed with 250 mg/kg of the active experimental Compounds E and G declined 47.0 mg/dL (p=0.0136) and 74.6 mg/dL (p=0.0023) from the baseline value. Fifty-four hours after the initial dosing, six hours after the third dosing, mean glucose levels of animals dosed with 125 mg/kg of the active experimental Compounds E and H declined 54.7 mg/dL (p<0.0001) and 33.3 mg/dL (p<0.0001), respectively, from baseline values. Fifty-four hours after the initial dosing, six hours after the third dosing, mean glucose levels of animals dosed with 125 mg/kg of the active experimental Compound G rose only 12.0 mg/dL (p=0.0071) from the baseline values.

125 mg/kg doses of Compound G suspended in vehicle also showed a trend in reducing plasma glucose relative to vehicle controls at thirty hours after initial oral administra-

TABLE 6

Effects of test substances on glucose-lowering in diabetic db/db mice.

| | Change in Glucose (mg/dL) | | Change in Glucose (mg/dL) | | Change in Glucose (mg/dL) | |
|---|---|---|---|---|---|---|
| | 6 H | P VALUE | 30 H | P VALUE | 54 H | P VALUE |
| Vehicle | 35.9 | | 79.6 | | 60.3 | |
| Metformin | −180.4 | <0.0001 | −112.4 | 0.0009 | −41.3 | 0.0696 |
| Compound C | −18.6 | NS | −40.7 | 0.0322 | 65.4 | NS |
| Compound C | −34.3 | 0.1287 | −69.7 | 0.0131 | −60.4 | 0.0409 |
| Compound C | −120.8 | 0.0019 | −221.4 | <0.0001 | −122.0 | 0.0086 |

*Statistical significance evaluated using unpaired t-test and Fisher's post-hoc test.
NS - not significant at p = 0.05 level

TABLE 7

Effects of test substances on body weights and food consumption in diabetic db/db mice.

| Dosage | TREATMENT | Body weight (g/mouse) (mean) 0 h | Body weight (g/mouse) (mean) 48 hr | Food Intake (g/mouse) 0–48 h |
|---|---|---|---|---|
| Vehicle | | 39.2 ± 0.5 | 39.5 ± 0.5 | 6.3 |
| 250 mg/kg | Metformin | 37.3 ± 0.7 | 37.2 ± 0.6 | 5.1 |
| 62.5 mg/kg | Compound C | 37.4 ± 0.4 | 38.2 ± 0.5 | 5.9 |
| 125 mg/kg | Compound C | 39.4 ± 0.4 | 39.7 ± 0.3 | 5.6 |
| 250 mg/kg | Compound C | 39.1 ± 0.8 | 38.4 ± 0.1 | 4.3 | tion. Thirty hours after initial dosing, mean glucose levels of the animals dosed with the active experimental Compound C suspended in vehicle declined 12.2 mg/dL (p=0.0926) from the baseline value.

By comparison, the known hypoglycemic agent metformin, given at 250 mg/kg, lowered plasma glucose levels by approximately 113.6 mg/dL (p<0.0001), six hours after the initial dose, and 25.1 mg/dL (p=0.0471), thirty hours after the initial dose, six hours after the second dose. At fifty-four hours after the initial dose, six hours after the third dose, glucose levels of animals given metformin at 250 mg/kg rose only 6.8 mg/dL (p=0.0033).

As shown in Table 9, below, the antihyperglycemic effect of Compounds E, G and H at dosage regimes of 125 mg/kg occurred in the absence of any significantly adverse effect on food intake or body weight. Body weights were not affected in animals treated during the test period (Table 9).The data in Tables 8 and 9 indicate that the aforementioned stilbenoids are effective hypoglycemic agents in a rodent model of insulin resistance, obesity, and NIDDM.

TABLE 8

Effects of test substances on glucose-lowering in diabetic db/db mice.

|  | Change in Glucose (mg/dL) | | Change in Glucose (mg/dL) | | Change in Glucose (mg/dL) | |
|---|---|---|---|---|---|---|
|  | 6 H | P VALUE | 30 H | P VALUE | 54 H | P VALUE |
| Vehicle | 15.5 |  | 56.6 |  | 88.6 |  |
| Metformin | −113.6 | <0.0001 | −25.1 | 0.0471 | 6.8 | 0.0033 |
| Compound E | −2.1 | NS | −47.0 | 0.0136 | −54.7 | <0.0001 |
| Compound G | 35.0 | NS | −12.2 | 0.0926 | 12.0 | 0.0071 |
| Compound H | 31.4 | NS | −74.6 | 0.0023 | −33.3 | <0.0001 |

*Statistical significance evaluated using unpaired t-test and Fisher's post-hoc test.
NS - not significant at p = 0.05 level

TABLE 9

Effects of test substances on body weights and food consumption in diabetic db/db mice.

| Dosage | TREATMENT | Body weight (g/mouse) (mean) 0 h | Body weight (g/mouse) (mean) 48 hr | Food Intake (g/mouse) 0–48 h |
|---|---|---|---|---|
|  | Vehicle | 39.8 ± 0.7 | 39.7 ± 0.6 | 6.0 |
| 250 mg/kg | Metformin | 40.6 ± 0.4 | 40.5 ± 0.4 | 5.4 |
| 125 mg/kg | Compound E | 39.5 ± 0.5 | 39.7 ± 0.6 | 5.7 |
| 125 mg/kg | Compound G | 39.0 ± 1.1 | 39.0 ± 1.1 | 5.9 |
| 125 mg/kg | Compound H | 38.7 ± 0.5 | 38.9 ± 0.5 | 5.6 |

Compounds A, D, E and F

Figure 6:
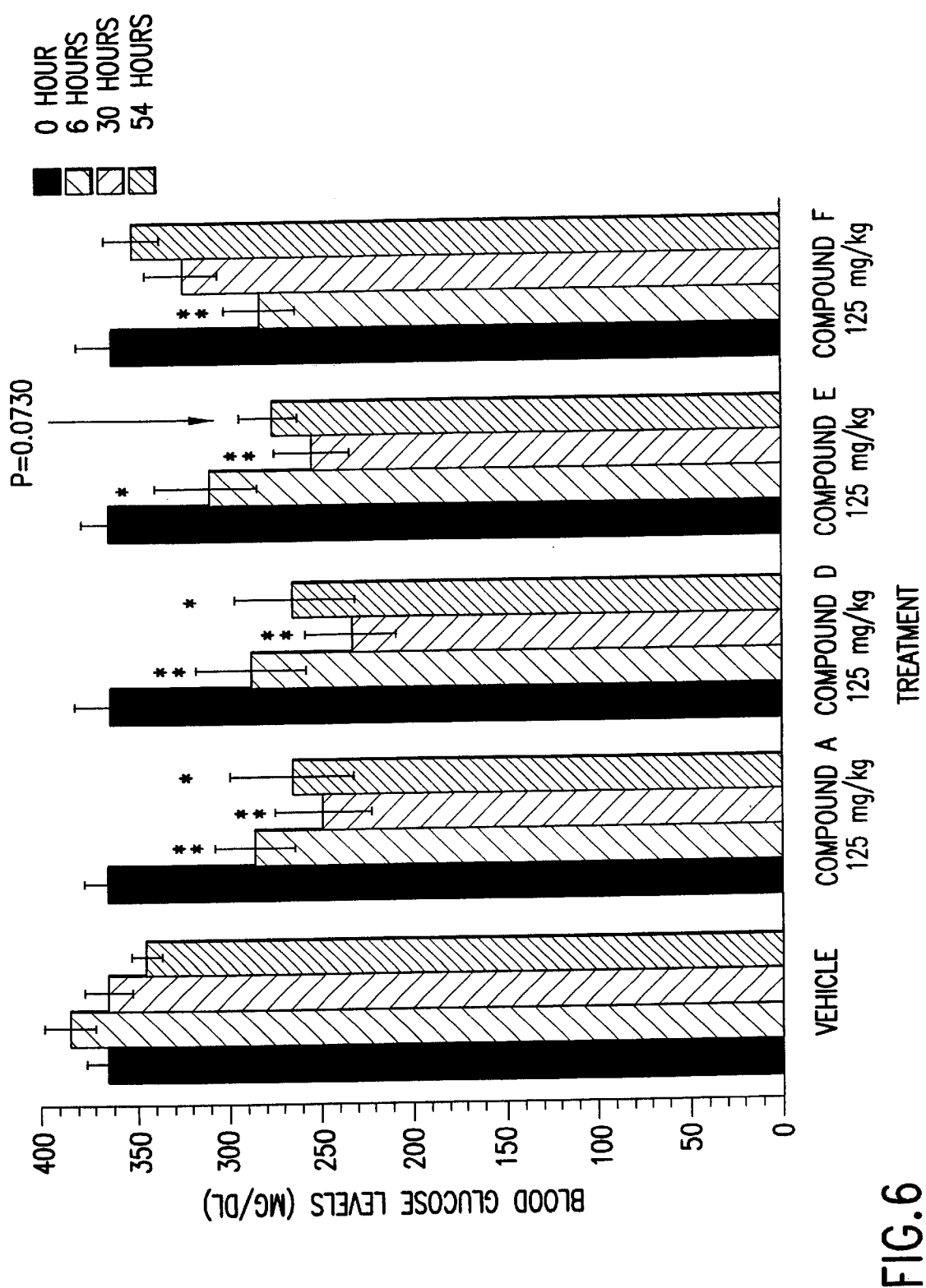
FIG. 6 is a bar graph showing the plasma glucose levels (mg/dL) of db/db mice treated with vehicle only; and 125 mg/kg q.d. of longistyline C (Compound A), 125 mg/kg q.d. of longistyline A (Compound D), 125 mg/kg q.d. of 7,8-dihydrolongistyline C (Compound E), and 125 mg/kg q.d. of 2″,3″,7,8-tetrahydrolongistyline C (Compound F). The relevant compound was administered to the animals at 0, 24 and 48 h, and plasma glucose levels were measured at 0, 6, 30 and 54 h. All data points N=8. *P<0.05; P<0.01; *P<0.0001 (analysis of variance (ANOVA); one factor).

As shown in FIG. 6 and in Table 10, below, oral administration of Compounds A (Longstyline C), D (Longstyline A), E (7,8-dihydrolongistyline C) and F (7,8,2",3"-tetrahydrolongistyline C) at a dose level of 125 mg/kg to db/db mice produced statistically significant reduction in plasma glucose, relative to vehicle (control).

The following test substances were evaluated in db/db mice for the ability to lower blood glucose: Compound A (Longstyline C), Compound D (Longstyline A), Compound E (7,8-dihydrolongistyline C) and Compound F (7,8,2",3"-tetrahydrolongistyline C). The test substances were evaluated in a series of experiments, which are summarized in Table 10 below.

Single doses of Compounds A (Longstyline C), D (Longstyline A), E (7,8-dihydrolongistyline C) and F (7,8, 2",3"-tetrahydrolongistyline C) were given to db/db mice at twenty-four and forty-eight hours after the initial oral administration resulted in statistically significant reductions in plasma glucose relative to vehicle controls at six, thirty or fifty-four hours or at all timepoints after oral administration. Six hours after the initial dosing, mean glucose levels of the animals dosed with 125 mg/kg of the active experimental Compounds A, D, E and F declined 78.5 mg/dL (p=0.0070), 76.4 mg/dL (p=0.0083), 53.8 mg/dL (p=0.0409) and 80.3 mg/dL (p=0.0062) from the baseline value. Thirty hours after the initial dosing, mean glucose levels of the animals dosed with 125 mg/kg of the active experimental Compounds A, D, and E declined 116.0 mg/dL (p=0.0008), 130.6 mg/dL (p=0.0002) and 109.9 mg/dL (p=0.0020) from the baseline value. Fifty-four hours after the initial dosing, six hours after the third dosing, mean glucose levels of animals dosed with 125 mg/kg of the active experimental Compounds A, D and E declined 99.2 mg/dL (p=0.0331) and 99.5 mg/dL (p=0.0277), respectively, from baseline values.

125 mg/kg doses of Compound E suspended in vehicle also showed a trend in reducing plasma glucose relative to vehicle controls at fifty-four hours after initial oral administration. Fifty-four hours after initial dosing, mean glucose levels of the animals dosed with the active experimental Compound E suspended in vehicle declined 86.6 mg/dL (p=0.0730) from the baseline value.

As shown in Table 11, below, the antihyperglycemic effect of Compounds A, E, G and H at dosage regimes of 125 mg/kg occurred in the absence of any significantly adverse effect on food intake or body weight. Body weights were not affected in animals treated during the test period (Table 11).

The data in Tables 11 indicate that the aforementioned stilbenoids are effective hypoglycemic agents in a rodent model of insulin resistance, obesity, and NIDDM.

TABLE 10

Effects of test substances on glucose-lowering in diabetic db/db mice.

|  | Change in Glucose (mg/dL) | | Change in Glucose (mg/dL) | | Change in Glucose (mg/dL) | |
|---|---|---|---|---|---|---|
|  | 6 H | P VALUE | 30 H | P VALUE | 54 H | P VALUE |
| Vehicle | 20.0 |  | 0.1 |  | −20.2 |  |
| Compound A | −78.5 | 0.0070 | −116.0 | 0.0008 | −99.2 | 0.0331 |
| Compound D | −76.4 | 0.0083 | −130.6 | 0.0002 | −99.5 | 0.0277 |
| Compound E | −53.8 | 0.0409 | −109.9 | 0.0020 | −86.6 | 0.0730 |
| Compound F | −80.3 | 0.0062 | −37.5 | NS | −10.2 | NS |

TABLE 10-continued

Effects of test substances on glucose-lowering in diabetic db/db mice.

| | Change in Glucose (mg/dL) | | Change in Glucose (mg/dL) | | Change in Glucose (mg/dL) | |
|---|---|---|---|---|---|---|
| | 6 H | P VALUE | 30 H | P VALUE | 54 H | P VALUE |

*Statistical significance evaluated using unpaired t-test and Fisher's post-hoc test.
NS - not significant at p = 0.05 level

TABLE 11

Effects of test substances on body weights and food consumption in diabetic db/db mice.

| Dosage | TREATMENT | Body weight (g/mouse) (mean) 0 h | Body weight (g/mouse) (mean) 48 hr | Food Intake (g/mouse) 0–48 h |
|---|---|---|---|---|
| | Vehicle | 39.4 ± 0.4 | 40.1 ± 0.4 | 6.1 |
| 125 mg/kg | Compound A | 40.3 ± 0.6 | 41.2 ± 0.6 | 6.0 |
| 125 mg/kg | Compound D | 39.3 ± 0.6 | 39.7 ± 0.7 | 5.7 |
| 125 mg/kg | Compound E | 39.6 ± 0.3 | 40.2 ± 0.4 | 5.7 |
| 125 mg/kg | Compound F | 39.3 ± 0.8 | 39.8 ± 0.8 | 5.8 |

The present invention is not to be limited in scope by the specific embodiments disclosed in the examples, which are intended as illustrations of a few aspects of the invention and any embodiments which are functionally equivalent are within the scope of this invention. Indeed, various modifications of the invention in addition to those shown and described herein will become apparent to those skilled in the art and are intended to fall within the appended claims.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

What is claimed is:

1. A method of lowering blood glucose in a mammal comprising administration to said mammal a pharmaceutical composition comprising a pharmaceutically acceptable carrier and a hypoglycemically effective amount of an isolated compound having the formula (I):

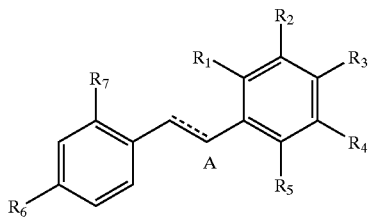

(I)

wherein,
A is selected from the group consisting of a single bond and a double bond in trans conformation;
$R_1$ is selected from the group consisting of H, OH, $C_{1-6}$alkoxy, COOH, and $COOC_{1-6}$alkyl;
$R_2$ is selected from the group consisting of H, OH, and $C_{1-10}$alkoxy;
$R_3$ is selected from the group consisting of H, $C_{1-10}$alkyl, $C_{2-10}$alkenyl, $C_{2-10}$alkynyl, and $C_{1-8}$cycloalkyl;
$R_4$ is selected from the group consisting of H, OH, and $C_{1-10}$alkoxy;
$R_5$ are selected from the group consisting of H, $C_{1-10}$alkyl, $C_{2-10}$alkenyl, $C_{2-10}$alkynyl, and $C_{1-8}$cycloalkyl;
$R_6$ is selected from the group consisting of H, OH, $C_{1-6}$alkoxy, COOH, and $COOC_{1-6}$alkyl;
$R_7$ is selected from the group consisting of H, OH, $C_{1-6}$alkoxy, COOH, and $COOC_{1-6}$alkyl; and
wherein at least one of $R_3$ and $R_5$ is selected from the group consisting of $C_{1-10}$alkyl, $C_{2-10}$alkenyl, $C_{2-10}$alkynyl, and $C_{1-8}$cycloalkyl;
or a pharmaceutically acceptable salt thereof.

2. The method of claim 1, wherein said hypoglycemically effective amount of said compound is about 1 to about 1000 mg/kg/day.

3. The method of claim 1, wherein said hypoglycemically effective amount of said compound is between about 50 to about 350 mg/kg/day.

4. The method of claim 1, wherein said composition is administered orally.

5. The method of claim 1, wherein said compound is isolated from *Cajanus cajan*.

6. The method of claim 1, wherein said pharmaceutically acceptable salt is selected from the group consisting of sodium, potassium, lithium, calcium, magnesium, zinc and iron.

7. The method of claim 1, wherein said mammal is suffering from diabetes.

8. The method of claim 1, wherein said mammal is suffering from hyperglycemia.

9. The method of claim 1, wherein said composition is administered in conjunction with another hypoglycemic agent selected from the group consisting of: an insulin; a biguanide; a sulfonylurea; a PPARγ agonist; an α-glucosidase inhibitor; and a β-adrenoceptor agonist.

10. A method of lowering blood glucose in a mammal comprising administration to said mammal a pharmaceutical composition comprising a pharmaceutically acceptable carrier and a hypoglycemically effective amount of an isolated compound selected from the group consisting of:
(A) Longistyline C;
(B) Longistyline A;
(C) longistyline A-6-carboxylic acid;
(D) 7,8-dihydrolongistyline C;
(E) 7,8,2",3"-tetrahydrolongistyline C;
(F) 7,8,2",3"-tetrahydrolongistyline A-6-carboxylic acid;
(G) 3-hydroxy-4isoprenyl-5-methoxystilbene-2-carboxylic acid;
(H) 3-hydroxy-4-(3-methylbutyl)-5-methoxy-7,8-dihydrostilbene-2-carboxylic acid;
(I) 4-isopentenylresveratrol (3,4',5-trihydroxy-4-(3-methyl-2-butenyl)stilbene;

(J) 3,5-dimethoxy-4-(3-methyl-2-butenyl)stilbene;
(K) 3,4',5-trimethoxy-4-(3-methyl-2-butenyl)stilbene;
(L) chlorophorin;
(M) 3,5-dimethoxy-4-(3-methyl-2-butenyl)bibenzene;
(N) 3,5-dihydroxy-4-(3-methyl-2-butenyl)bibenzene;
(O) 3,5-dihydroxy-4-(3-methyl-2-butenyl)bibenzyl-2-carboxylic acid;
(P) 3-hydroxy-5-methoxy-4-(3-methyl-2-butenyl)bibenzene;
(Q) 5-hydroxy-3-methoxy-4-(3-methyl-2-butenyl)bibenzene;
(R) 3,5-dihydroxy-2-(3-methyl1-2-butenyl1)bibenzene;
(S) 3-hydroxy-5-methoxy-2-(3-methyl-2-butenyl)bibenzene;
(T) 5-hydroxy-3-methoxy-2-(3-methyl-2-butenyl)bibenzene;
(U) 3,5-dihydroxy-4-(3,7-dimethyl-2,6-octadienyl)-bibenzene;
(V) 3,5-dimethoxy-4-(3,7-dimethyl-2,6-octadienyl)-bibenzene;
(W) 3,5-diacetyl-4-(3,7-dimethyl-2,6-octadienyl)-bibenzene;
(X) 3,4',5-trihydroxy4-(3,7-dimethyl-2,6-octadienyl)-bibenzene;
(Y) 3,5-dihydroxy-4-(3,7-dimethyloctyl)bibenzene;
(Z) 3,5-dimethoxy-4-(3,7-dimethyloctyl)bibenzene;
(AA) 2-geranyl-3,5-dihydroxybibenzene;
(AB) 2-geranyl-3,5-dimethoxybibenzene;
(AC) 2-geranyl-3-hydroxy-5-methoxybibenzene; and
(AD) 3-methoxy-4'-hydroxy-4-(3-methyl-2-butenyl)bibenzene.

11. The method of claim 10, wherein said compound is selected from the group consisting of:

(1)-Longistyline C (Cmd.A);

(2)-Longistyline A (Cmd.C); and (3)-longistyline A-6-carboxylic acid (Cmd.D).

* * * * *